(12) United States Patent
Arakelyan et al.

(10) Patent No.: US 7,970,550 B2
(45) Date of Patent: Jun. 28, 2011

(54) INTERACTIVE TECHNIQUE FOR OPTIMIZING DRUG DEVELOPMENT FROM THE PRE-CLINICAL PHASES THROUGH PHASE-IV

(75) Inventors: Levon Arakelyan, Ashdod (IL); Vera Selitser, Jerusalem (IL); Zvia Agur, Tel Aviv (IL)

(73) Assignee: Optimata, Ltd, Ramat Gan (IL)

( * ) Notice: Subject to any disclaimer, the term of this patent is extended or adjusted under 35 U.S.C. 154(b) by 438 days.

(21) Appl. No.: 10/662,345

(22) Filed: Sep. 16, 2003

(65) Prior Publication Data
US 2004/0107084 A1    Jun. 3, 2004

Related U.S. Application Data

(60) Provisional application No. 60/410,803, filed on Sep. 16, 2002.

(51) Int. Cl.
G06F 19/00    (2006.01)
(52) U.S. Cl. ......................................................... 702/19
(58) Field of Classification Search ........................ None
See application file for complete search history.

(56) References Cited

U.S. PATENT DOCUMENTS

| | | |
|---|---|---|
| 5,657,255 A | 8/1997 | Fink et al. |
| 5,808,918 A | 9/1998 | Fink et al. |
| 6,041,788 A | 3/2000 | Shen |
| 6,081,786 A | 6/2000 | Barry et al. |

FOREIGN PATENT DOCUMENTS

| | | |
|---|---|---|
| WO | WO 97/44752 A1 | 11/1997 |
| WO | WO 01/00083 A1 | 1/2001 |
| WO | WO 02/051354 A2 | 7/2002 |

OTHER PUBLICATIONS

Holford et al. (Ann. Rev. Pharmacol. Toxicol. (2000) vol. 40, pp. 209-234).*
Rooney et al. (DDT (2001). vol. 6, No. 5, pp. 802-806).*
FDA, Center for Drug Evaluation and Research (CDER), Drug Development Process for Investigational New Drugs, http://www.fda.gov/cder/handbook/develop.htm, pp. 3-28, Revised Mar. 6, 1998.
Department of Health and Human Services, FDA, International Conference on Harmonization: Guidance on General Considerations for Clinical Trials, Federal Register Wednesday, Dec. 17, 1997, pp. 66113-66119, vol. 62, No. 242.
E.A. Eisenhauer et al, Phase-I clinical trial design in cancer drug development, J Clin Oncol, Feb. 2000, pp. 684-692, vol. 18(3).
R. Simon et al, Accelerated titration designs for Phase-I clinical trials in oncology, J Natl Cancer Inst, Aug. 6, 1997, pp. 1138-1147, vol. 89(15).
J.M. Collins et al, Potential roles for pre-clinical pharmacology in Phase-I clinical trials, Cancer Treat Rep, Jan. 1986, pp. 73-80, vol. 70(1).
Z. Agur et al, Effect of the dosing interval on survival and myelotoxicity in mice treated by Cytosine arabinoside, Eur. J. Cancer, 1992, pp. 1085-1090, vol. 28A(6/7).
L. Cojocaru et al, Theoretical analysis of interval drug dosing for cell-cycle-phase-specific drugs, Math. Biosci., 1992, pp. 85-97, vol. 109.
P. Ubezio et al, Increasing 1-b-D-Arabinofuranosylcytosine efficacy by scheduled dosing intervals based on direct measurement of bone marrow cell kinetics, Cancer Res, 1994, pp. 6446-6451, vol. 54.
Z. Agur, Resonance and anti-resonance in the design of chemotherapeutic schedules. Jour. Theor. Medicine, 1998, pp. 237-245, vol. 1.
Z. Agur, Clinical trials of Zidovudine in HIV infection, Lancet, Dec. 9, 1989, p. 1400, vol. 2(8676).
Z. Agur, Use of mathematical models for analyzing host-specific parasitaemia profiles in African trypanosomes, Parasitology Today, 1992, pp. 128-129, vol. 8.
R. Norel et al, A model for the adjustment of the mitotic clock by cyclin and MPF levels. Science, 1991, pp. 1076-1078, vol. 251.
Z. Agur et al, Zidovudine toxicity to murine bone marrow may be affected by the exact frequency of drug administration, Exp. Hematol, 1991, pp. 364-368, vol. 19.
Z. Agur, Fixed points of majority rule cellular automata applied to plasticity and precision of the immune response, Complex Systems, 1991, pp. 351-356, vol. 5.
Z. Agur et al, Maturation of the humoral immune response as an optimization problem, Proc. R. Soc. Lond. B, 1991, pp. 147-150, vol. 245.
L.H. Harnevo et al, Drug resistance as a dynamic process in a model for multi-step gene amplification under various levels of selection stringency, Cancer Chemo Pharmacol, 1992, pp. 469-476, vol. 30.
R. Mehr et al, Bone marrow regeneration under cytotoxic drug regimens: behaviour ranging from homeostasis to unpredictability in a model for hemopoietic differentiation, BioSystems, 1992, pp. 231-237, vol. 26/4.
Z. Agur et al, Pulse mass Measles vaccination across age cohorts, Proc. Nat. Acad. Sci. USA, 1993, pp. 11698-11702, vol. 90.
Z. Agur et al, Use of knowledge on {fn} series for predicting optimal chemotherapy treatment, Random & Computational Dynamics, 1994, pp. 279-286, vol. 2(3&4).
Z. Agur et al, AZT effect on the Bone Marrow—a new perspective on the Concorde Trials, Jour. Biol. Sys, 1995, pp. 241-251, vol. 3(1).
R. Mehr et al, Temporal stochasticity leads to nondeterministic chaos in a model for blood cell production. in: "Fluctuations and Order:The New Synthesis", 1996, pp. 419-427, Springer, New-York.
D. Hart et al, The growth law of primary breast cancer tumors as inferred from mammography screening trials, Br J Can, 1998, pp. 382-387, vol. 78(3).

(Continued)

Primary Examiner — Lori A Clow
(74) Attorney, Agent, or Firm — Sughrue Mion, PLLC

(57) ABSTRACT

A method of performing interactive clinical trials for testing a new drug. A pre-clinical phase is performed in which a computer model for pharmacokinetics and pharmacodynamics of the drug is created and adjusted based on in vitro studies and in vivo studies in animals. A phase I clinical research is performed in which a clinical trial on at least a single dose is performed in parallel with performing computer simulation studies using the computer model. An optimal protocol is determined for the most responsive patient populations and indications for a phase II clinical trial. Phase II clinical trial is performed where a number of small scale clinical trials are performed in parallel based on results of the above. Phase III clinical research is performed for chosen indications by chosen protocols. Phase IV studies are performed for post-marketing subpopulation analysis and long term product safety assessment.

21 Claims, 22 Drawing Sheets

OTHER PUBLICATIONS

E. Shochat et al, Using Computer Simulations for Evaluating The Efficacy of Breast Cancer Chemotherapy Protocols, Math. Models & Methods in Applied Sciences, 1999, pp. 599-615, vol. 9(4).

K. Skomorovski et al, New TPO treatment schedules of increased safety and efficacy: pre-clinical validation of a thrombopoiesis simulation model, Br J Haematol, Nov. 2003, pp. 683-691, vol. 123(4).

L. Arakelyan et al, A computer algorithm describing angiogenesis and vessel maturation and its use for studying the effects of anti-angiogenic and anti-maturation therapy on vascular tumor growth, Angiogenesis, 2002, pp. 203-214, vol. 5.

R. Simon, Bayesian design and analysis of active controlled clinical trials, Biometrics, 1999, pp. 484-487, vol. 55.

R. Simon, Some practical aspects of the interim monitoring of clinical trials, Statistics in Medicine, 1994, pp. 1401-1409, vol. 13.

R. Simon, Therapeutic equivalence trials, Handbook of Statistics in Clinical Oncology, 2001, pp. 173-187, Marcel Dekker, New York.

A. Iliadis et al, Optimizing Drug Regimens in Cancer Chemotherapy by an Efficacy-Toxicity Mathematical Model, Computers and Biomedical Research, 2000, pp. 211-226, vol. 33.

F.L. Pereira et al, A new optimization based approach to experimental combination chemotherapy, Frontiers Med Biol Engng, 1995, pp. 257-268, vol. 6(4).

C. Veyrat-Follet et al, Clinical trial simulation of docetaxel in patients with cancer as a tool for dosage optimization, Clin Pharmacol Ther, Dec. 2000, pp. 677-687 vol. 68/6.

RS Acharya, et al, Development of optimal drug administration strategies for cancer-chemotherapy in the framework of systems theory, Int J Biomed Comput, Mar.-Apr. 1984, pp. 139-150, vol. 15(2).

N. Stallard et al, Sequential designs for phase III clinical trials incorporating treatment selection, Stat Med, Mar. 2003, pp. 689-703, vol. 22(5).

JV Gobburu et al, Application of modeling and simulation to integrate clinical pharmacology knowledge across a new drug application, Int J Clin Pharmacol Ther, Jul. 2002, pp. 281-288,—vol. 40(7).

P. Bauer et al, Combining different phases in the development of medical treatments within a single trial, Stat Med, Jul. 1999, pp. 1833-1848, vol. 18(14).

E. Ardizzone et al, Artificial intelligence techniques for cancer treatment planning, Med Inform (Lond), Jul.-Sep. 1988, pp. 199-210, vol. 13(3).

D. Berry, Adaptive Trials and Bayesian Statistics in Drug Development, Biopharmaceutical Report, 2001, pp. 1-11 vol. 9(2).

D. Berry, General Keynote: Clinical Trial Design, Gynecological Oncology, 2003, pp. S114-S116, vol. 88.

E. Trimble, Discussion: Current Issues in the Design of Ovarian Cancer Treatment Trials, Gynecological Oncology, 2003, pp. S122-S123, vol. 88.

Z. Agur, "Mathematical modeling of cancer chemotherapy: investigation of the resonance phenomenon", Adv. in Math. Pop Dynamics-Molecules, Cells, Man, Series in Math. Biol., 1998, (6)543-555.

* cited by examiner

INTERACTIVE TECHNIQUE FOR OPTIMIZING DRUG DEVELOPMENT FROM THE PRE-CLINICAL PHASES THROUGH PHASE-IV

RELATED APPLICATIONS

This Application claims priority from U.S. provisional Application Ser. No. 60/410,803 filed Sep. 16, 2002, the contents of which are incorporated herein by reference. The disclosure of U.S. application Ser. No. 09/691,053, filed Oct. 19, 2000, now U.S. Pat. No. 6,871,171, is also incorporated herein by reference.

FIELD

The disclosed teachings relate to an interactive technique for performing the testing of a new drug and its development from phase I-phase IV testing.

BACKGROUND

1. References

The following papers provide useful background information, for which they are incorporated herein by reference in their entirety, and are selectively referred to in the remainder of this disclosure by their accompanying reference keyword in square brackets (i.e., 3. for the reference by Dodion et al.)

1. Drug Development Process for Investigational New Drugs. FDA Center for Drug Evaluation and Research (CDER). http://www at the site fda.gov/cder/handbook/develop.htm
2. Department Of Health And Human Services, Food and Drug Administration. International Conference on Harmonization; Guidance on General Considerations for Clinical Trials. Federal Register/Vol. 62, No. 242/Wednesday, Dec. 17, 1997.
3. Dodion P, Kenis Y, Staquet M. Phase-I trials of single agents in adult solid tumours: preclinical and clinical aspects. Drugs Exp Clin Res 1986; 12(1-3):23-30.
4. Fridborg H, Nygren P, Larsson R. Relationship between pharmacokinetic parameters in patients and cytotoxicity in vitro of standard and investigational anticancer drugs. Anticancer Drugs 1995 February; 6(1):64-9.
5. Eisenhauer E A, O'Dwyer P J, Christian M, Humphrey J S. Phase-I clinical trial design in cancer drug development. J Clin Oncol 2000 February; 18(3):684-92
6. Simon R, Freidlin B, Rubinstein L, Arbuck S G, Collins J, Christian M C. Accelerated titration designs for Phase-I clinical trials in oncology. J Natl Cancer Inst 1997 Aug. 6; 89(15):1138-47.
7. Collins J M, Zaharko D S, Dedrick R L, Chabner B A. Potential roles for preclinical pharmacology in Phase-I clinical trials. Cancer Treat Rep 1986 January; 70(1):73-80.
8. Agur Z., Arnon R., Schechter B. Effect of the dosing interval on survival and myelotoxicity in mice treated by Cytosine arabinoside. Eur. J. Cancer., 28A(6/7), 1992 (pp. 1085-1090).
9. Cojocaru L., Agur Z. Theoretical analysis of interval drug dosing for cell-cycle-phase-specific drugs. Math. Biosci., 109, 1992 (pp. 85-97).
10. Ubezio P., Tagliabue G., Schechter B., Agur Z. Increasing 1-b-D-Arabinofuranosylcytosine efficacy by scheduled dosing intervals based on direct measurement of bone marrow cell kinetics, Cancer Res 54, 1994 (pp. 6446-6451).
11. Agur Z. Resonance and anti-resonance in the design of chemotherapeutic schedules. Jour. Theor. Medicine 1, 1998 (pp. 237-245).
12. Agur Z. Clinical trials of Zidovudine in HIV infection. Lancet 2, 1989, (p. 734).
13. Agur Z. Use of mathematical models for analyzing host-specific parasitaemia profiles in African trypanosomes. Parasitology Today 8, 1992 (pp. 128-129).
14. Norel R., Agur Z. A model for the adjustment of the mitotic clock by cyclin and MPF levels. Science, 251, 1991 (pp. 1076-1078).
15. Agur Z., Arnon R., Sandak B., Schechter, B. Zidovudine toxicity to murine bone marrow may be affected by the exact frequency of drug administration. Exp. Hematol., 19, 1991 (pp. 364-368).
16. Agur Z. Fixed points of majority rule cellular automata applied to plasticity and precision of the immune response. Complex Systems, 5, 1991 (pp. 351-356).
17. Agur Z., Mazor G., Meilijson I. Maturation of the humoral immune response as an optimization problem. Proc. R. Soc. Lond. B, 245, 1991 (pp. 147-150).
18. Harnevo L. H., Agur Z. Drug resistance as a dynamic process in a model for multi-step gene amplification under various levels of selection stringency. Cancer Chemo. Pharmacol., 30, 1992 (pp. 469-476).
19. Mehr R., Agur Z. Bone marrow regeneration under cytotoxic drug regimens: behaviour ranging from homeostasis to unpredictability in a model for hemopoietic differentiation. BioSystems, 26/4, 1992 (pp. 231-237).
20. Agur Z., Cojocaru L., Mazor G., Anderson R. M., Danon Y. L. Pulse mass Measles vaccination across age cohorts Proc. Nat. Acad. Sci. USA, 90, 1993 (pp. 11698-11702).
21. Agur Z., Dvir Y. Use of knowledge on {□n} series for predicting optimal chemotherapy treatment. Random & Computational Dynamics 2(3&4), 1994 (pp. 279-286).
22. Agur Z., Tagliabue G., Schechter B., Ubezio P. AZT effect on the Bone Marrow—a new perspective on the Concorde Trials. Jour. Biol. Sys 3(1), 1995 (pp. 241-251).
23. Mehr R., Agur Z. Temporal stochasticity leads to nondeterministic chaos in a model for blood cell production. p. 419-427 in: Fluctuations and Order: The New Synthesis. (M. M. Millonas ed.) New-York, Springer. 1996.
24. Agur, Z. Mathematical modelling of cancer chemotherapy: investigation of the resonance phenomenon. Advances in Math. Pop Dynamics—Molecules Cells, Man, Series in Math. Biol: (Kimmel and Arino eds) 6, 1998 (pp 543-555).
25. Hart D., Shochat, E.& Agur, Z. The growth law of primary breast cancer tumors as inferred from mammography screening trials. British Journal of Cancer, 78 (3) 1998 (pp. 382-387).
26. Shochat, E. Hart, D & Agur, Z. Using Computer Simulations for Evaluating The Efficacy of Breast Cancer Chemotherapy Protocols Jour. Math. Models & Methods in Applied Sciences Vol. 9 (4) 1999 (pp. 599-615).
27. Agur, Z. Hassin, R and Levy, S. Optimizing chemotherapy scheduling using local search heuristics. In Press.
28. Skomorovski K, Vardi M Harpak, H, Visser T P, Wagemaker G and Agur Z. Improved thrombopoietin treatment schedules—preclinical validation of a computational tool, The British Journal of Haematology, in press.
29. Arakelyan L, Vainstain V, and Agur Z. A computer algorithm describing angiogenesis and vessel maturation and its use for studying the effects of anti-angiogenic and anti-maturation therapy on vascular tumor growth. Angiogenesis. May 2002 (pp. 203-214).

30. Simon R. Bayesian design and analysis of active controlled clinical trials. Biometrics 1999; 55:484-487
31. Simon R. Some practical aspects of the interim monitoring of clinical trials. Statistics in Medicine 1994; 13:1401-1409
32. Simon R. Therapeutic equivalence trials. Handbook of Statistics in Clinical Oncology 2001; 173-188

2. Introduction

The drug industry is facing substantial challenges with regards to cost-containment and time-to-market for its high-potential candidates. Currently pharmaceutical companies investigate many different methods for increasing their productivity in the development process in order to compensate for increasing difficulties in recouping the investment in drug development.

However, the classical method of clinical trials design [1,2] suffers major drawbacks. On the one hand, developing drugs by "trial and error" alone can not guarantee that the selected schedules are better than other, yet to be tried, treatment regimens. On the other hand, the number of schedules which can be empirically tested is negligibly small with respect to the potential number of sensible schedules.

Research shows that the effects of the drug may crucially correlate with the internal dynamics of the tumor growth processes, as well as with the relevant patient's physiology. These aspects might often be too complex to be estimated by the naked eye, and slight nuances in the treatment schedule may be critical for the effect achieved [8-11]. In theory, if all potential treatment schedules could be tested, considering all the available information on the involved biological processes, pathological processes and the momentary effect of the drug on every element of these processes, one could, a-priori, suggest a theoretical set of the most promising treatment schedules for a given indication, or, even, for a given patient. Subsequently, these promising schedules would be clinically tested, thus saving human resources and time, and helping to achieve maximal possible therapeutic effects of the tested drug.

Needless to say that such methods would enable to rehabilitate drugs with valid properties, which failed during the development process, due to insufficient efficacy, or limitations of toxicity, which could possibly be overcome by modifying the treatment schedule. In addition, these methods would enable a "Go-NoGo" decision to be made early during the clinical trial process.

3. Definitions and Notations

For ease of understanding of the present specification, the following abbreviations/notations are used:

$A_1$-$A_3$—constants
$B_1$-$B_3$—constants
BL—blood
c—elevation increment of drug concentration
$C_{Di}$—the concentration after administrating the given dose in blood
$C_{Dij}$—the concentration after administering the given dose "i" in target tissue
$C_{Dik}$—the concentration after administering the given dose "i" in toxicity tissue "k"
$C_f$—drug concentration
CmC—a control group for combinational therapy (patients treated by today's first line therapy)
CT—clinical trial
d—elevation increment of the drug dose
$D_0$(PhI)—initial dose proposed for Phase I clinical trial
$D_i$—dose administered
DLT—dose-limiting toxicity
$D_n$—dose for a given variant of the protocol proposed by the model for testing
$D_o$-$D_f$—initial dose to final dose,
EC—effective concentration
$E_{ci}$—effect of the drug at the given concentration
$E_{cij}$—effect of the drug at the given concentration "i" on target tissue "j"
$E_{Cdik}$—effect of the drug at the administered dose "i" on toxicity tissue "k"
$EC_n$—effective concentration n, the concentration giving n percent of maximal effect
ED—effective dose
$E_{Dij}$—the efficacy after administering the given dose "i" in target tissue "j"
F1, F2, F3—counters
$G_o$—a rationale to continue developing the drug
Group Ci—group of patients for combinational treatment by protocol I (CTPi) for indication cancer type I (CTi)
Group Mi—group of patients for monotherapy treatment by protocol I (MTPi) for indication cancer type I (CTi)
h—of human tissue/cell culture
$h_{tc}$—human tumor cells
K1, K2—counters
$LD_n$—lethal dose n, i.e. a dose causing n percent of death in the tested animals group
MA, MB, MC—number of tests in which the drug effect remains<X, when escalating concentrations, for stopping further dose escalation
MED—Minimum Effective Dose, a dose at which the effect was first observed
MnC—a standard monotherapy treatment group (patients treated by today's first line therapy)
MTD—maximal tolerated dose (after which the DLT is observed)
$n_1$—number of steps to be defined in order to going from mED to MTD;
$n_2$—number of steps to be defined to go from mED to RD
nr—nonrodent species
NO GO—no rationale to continue developing the drug.
P—percent of animals that died
PD—pharmacodynamics
PK—pharmacokinetics
r—of rodent tissue/cell culture
$r/h_{Tox}$—rodent or human toxicity
$r_{tc}$—rodent tumor cells
RD—recommended dose
$S_1$-$S_2$—constants
$T_n$—dose interval for a given variant of the protocol proposed by the model for testing
Tox—the tissue in which a toxic effect occurs ("toxicity" tissue)
TT—target tissue
VPE—Virtual Patient Engine
X—accepted threshold ("asymptote") of differences in the effect after elevation of concentration by one increment (c).
Z1, Z2, Z3—counters

SUMMARY

To realize advantages noted above, there is provided a method of performing interactive clinical trials for testing a new drug comprising performing a pre-clinical phase in which a computer model for pharmacokinetics and pharmacodynamics of the drug is created and adjusted based on in vitro studies and in vivo studies in animals. A phase I clinical research is performed in which a clinical trial on at least a single dose is performed in parallel with performing computer simulation studies using the computer model. The computer model is adjusted based on comparison of the results of the clinical research and the computer simulation. A maximal tolerated dose, minimum effective dose, and a recommended dose is determined based on the phase I clinical research in conjunction with the computer simulations. The drug is checked for cumulative effects and providing this information to the computer model. Multiple simulations are performed using the computer model with different doses and dosing intervals. An optimal protocol is determined for the most responsive patient populations and indications for a phase II clinical trial. Phase II clinical trial is performed where a number of small scale clinical trials are performed in parallel based on results of the above. The interim results are analyzed to choose the most promising regimens for continued clinical trials. Phase III clinical research is performed for chosen indications by chosen protocols. Phase IV studies are performed for post-marketing subpopulation analysis and long term product safety assessment.

In a specific enhancement during phase I studies, prior to each sub-step of the phase I trial, computer simulation is performed to predict results of the sub-step and the predicted results are compared to clinical results corresponding to the sub-step and the computer model is adjusted based on the comparison.

In another specific enhancement, a first decision whether to continue with the trial is made, stopping the trial if an adverse decision is made.

In another specific enhancement, the results of determination of the optimal protocol are used to define indications and define sub-groups of patients most sensitive, susceptible and responsive to the drug.

More specifically, effective treatment protocol is defined for a subset of the subgroups.

In yet another specific enhancement the computer model is adjusted based on whether the clinical research indicates a result higher than a threshold in at least one of pre-clinical, phase I and phase II studies.

In still another specific enhancement during phase II trial, small clinical trials are performed in parallel for a chosen indication by a chosen treatment protocol.

In still another specific enhancement, in analyzing interim results, the most promising trials are chosen for indications most sensitive to the drug administered via the most efficient protocol.

More specifically, in analyzing interim results, a second decision whether to continue with the trial is made, stopping the trial if an adverse decision is made.

Even more specifically the second decision is based on a prediction of safety profile of the new drug in the most promising trial compared with safety of pre-existing therapies.

Still more specifically, the second decision is based on a prediction of efficacy profile of the new drug in the most promising trial compared with efficacy of pre-existing therapies.

In yet another specific enhancement, phase III clinical research is performed to prove safety of the drug.

In yet another specific enhancement, phase IV clinical research is performed to prove efficacy of the drug.

In still another specific enhancement, when hitherto unknown effects are discovered, the computer model is adjusted to obtain predictions for new protocols, patient populations and indications.

Another aspect of the disclosed teachings is a method of performing interactive clinical trials for a new drug comprising a step of performing a pre-clinical phase in which a computer model for pharmacokinetics and pharmacodynamics is created and adjusted based on in vitro studies and in vivo studies in animals.

Still another aspect of the disclosed teachings is a method of performing interactive clinical trial for a new drug comprising a step of performing a phase I clinical trial wherein a dose-escalation trial is performed in parallel with computer simulation studies to predict results and the prediction is compared with clinical results and the comparing is used to adjust the computer model.

Still another aspect of the disclosed teachings is a method of performing interactive clinical trials for a new drug comprising developing a strategy for a next sub-step in phase I clinical trial in conjunction with simulated computer predictions.

BRIEF DESCRIPTION OF THE DRAWINGS

The disclosed teachings will become more apparent by describing in detail examples and embodiments thereof with reference to the attached drawings in which:

FIG. 5I shows an example of a computer simulation between Phase I and Phase II.

DETAILED DESCRIPTION

Synopsis

Today, there exist elaborate and highly interdisciplinary and multidisciplinary methods, which can employ modern computing facilities for integrating the enormous body of relevant biological, medical, pharmacological and mathematical (dynamical) information into comprehensive systems for simulating different drug treatment scenarios. The techniques disclosed herein are based on more than two decades of biomathematical research in the area of disease control optimization [8-28]. Thus, mathematical algorithms have been developed, which simulate the dynamics of key biological, pathological and pharmacological processes in a patient undergoing drug treatment, either by monotherapy, or by combination of cytotoxic and/or cytostatic agents, and/or by growth-factors. This set of computerized mathematical models, in conjunction with advanced optimization algorithms have now yielded an in silico patient engine, having a range of applications designed to deliver optimal drug treatments for cancer and hematological disorders [eg., 28-29].

Disclosed herein are techniques for improving anticancer drug development, which employ such an in silico patient engine in drug development. The disclosed techniques enable the drug developer an ongoing dialogue, from pre-clinical phase through Phase-IV, for generating, fine-tuning and validating a reliable drug/disease/host model. Thus, relatively early during development, i.e., by the end of Phase-I, and no later than in mid-Phase-II, the model already contains the precise PK/PD drug parameters, to be implemented in the in silico patient simulations. At this stage numerous drug schedules (termed "infinite protocol space") are simulated for any desired indication, and proprietary optimization techniques are employed for selecting, among the vast number of simulation scenarios, those yielding best results according to the list of specifications set by the drug developer. In this way one identifies the most appropriate indications/monotherapy/combination treatments for the drug. At this early stage a "Go-NoGo" decision can be made.

Following the disclosed techniques clinical trials can be rationally designed, which will be based upon a gradual improvement and zeroing-in on the best prediction-directed treatment schedules. It is important to stress that the disclosed technique carries little risk of yielding false predictions, since the algorithm has been designed so as to be continuously validated and improved by information derived in parallel from clinical trials.

Figure 6:
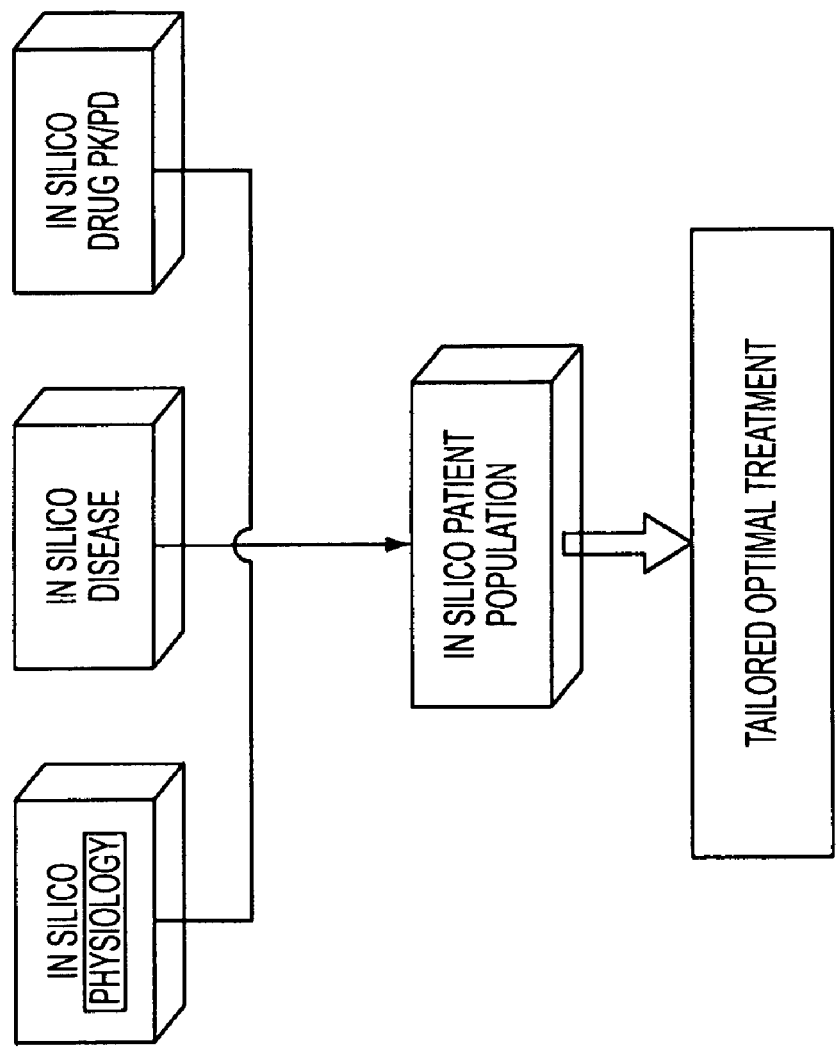
FIG. 6 shows an example of an overall framework for treatment optimization.

An overall framework for treatment optimization is shown in FIG. 6. In the In Silico Patient modules mathematical algorithms for disease process, physiological processes & drug PK/PD are computerized. In the treatment Optimization Module—optimal treatments satisfying user's (eg., Pharma) specifications are predicted.

ILLUSTRATIVE EXAMPLE

Figure 4:
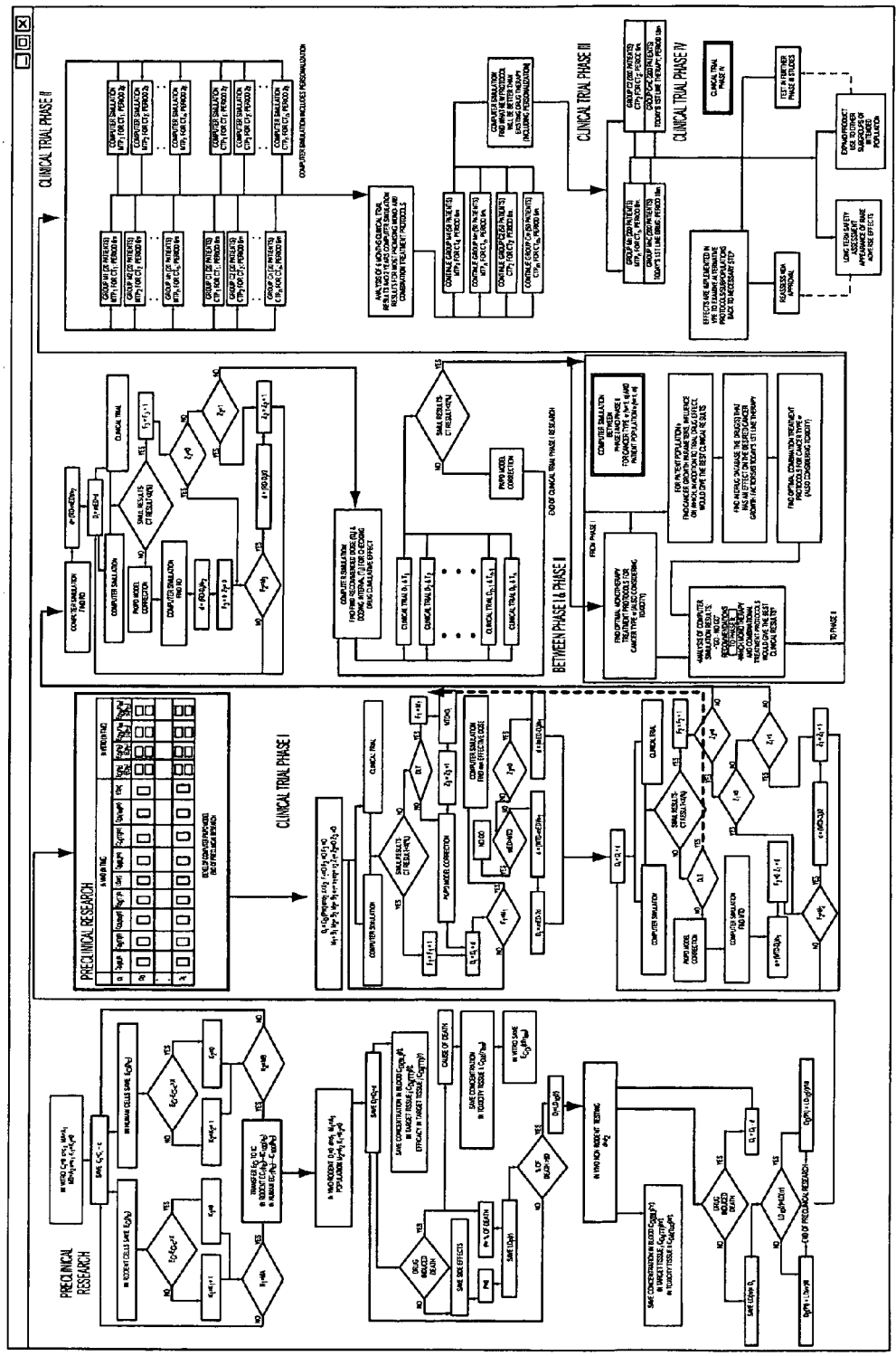
FIG. 4 shows an overall diagram of an example implementation of the disclosed interactive clinical trial technique

FIG. 4 shows an example implementation of the disclosed techniques. It should be noted that the scope of the disclosed technique is not limited specifically to this example implementation which is merely illustrative and exemplary in nature.

1. Pre-Clinical Phase: Constructing the PK/PD Module

The pre-clinical phase of drug development is dedicated to retrieval of the drug's pharmacodynamics (PD) and pharmacokinetics (PK) in animals and to initializing human PD research. In this phase the computer model is adjusted to the drug under development, as is detailed below.

Based on the in vitro studies the drug PD module is constructed. Putative mechanisms of drug action are simulated, retrieving the most appropriate mechanism in the animal trials. From the results of the in vitro studies, the parameters of drug's effect on the different target tissues are empirically estimated and inputted into the module. These include the data of experiments using different tumor types, possibly in combination with another drug. Inversely, the model here can simulate and comparatively estimate the efficacy of the treatment in combination with other known drugs, as well as the effect of the drug on different tumor types. In this way the pre-clinical research can be directed to the most effective avenues. The model is continuously fine-tuned, by "on-line" implementation in the In Silico Patient, of the pre-clinical research results. Thus, the model interactively guides the empirical research to reveal the further necessary data.

Using animal studies, the PK module is adjusted to describe the PK of the given drug. The PD module, which until now was based on the in vitro data only, is adjusted to represent the in vivo results, and is supplemented with animal parameters for the functions of drug effect time series. This, again, includes data on different tumor types and on the effects of combinations with other drugs. From animals treated by multiple doses, some data on cumulative effect can be obtained and implemented in the model.

The toxicity module is designed to include the qualitative and quantitative data on the side effects observed during the animal studies. In this way the module describing hemopoietic processes is provided with parameters of the drug effect on hemopoiesis, if observed in animals; other toxicities observed are described as a function of the drug time course. From animals treated by multiple doses, some data on cumulative toxicity may be obtained and implemented in the model as well.

At this stage the model already has the capacity to make approximate predictions on the administration of the drug to humans. Known inter-species differences in the effected tissue characteristics are taken into account when simulating the human PK model, in order to consider a reasonable dose range for Phase-I human studies. That procedure is expected to offer an improvement of the traditional LD10/10 initial dose for Phase-I trials, which is often too low to have any effect on the disease. That is to say that already in this stage, based on in vitro and in vivo data the model can be used for predicting the minimal dose within therapeutic range, i.e. the lowest dose, which has a rationale to be tested. It is possible at this point to use the model for predicting failure of the drugs with therapeutic doses too toxic to be tolerated.

Figure 5A:
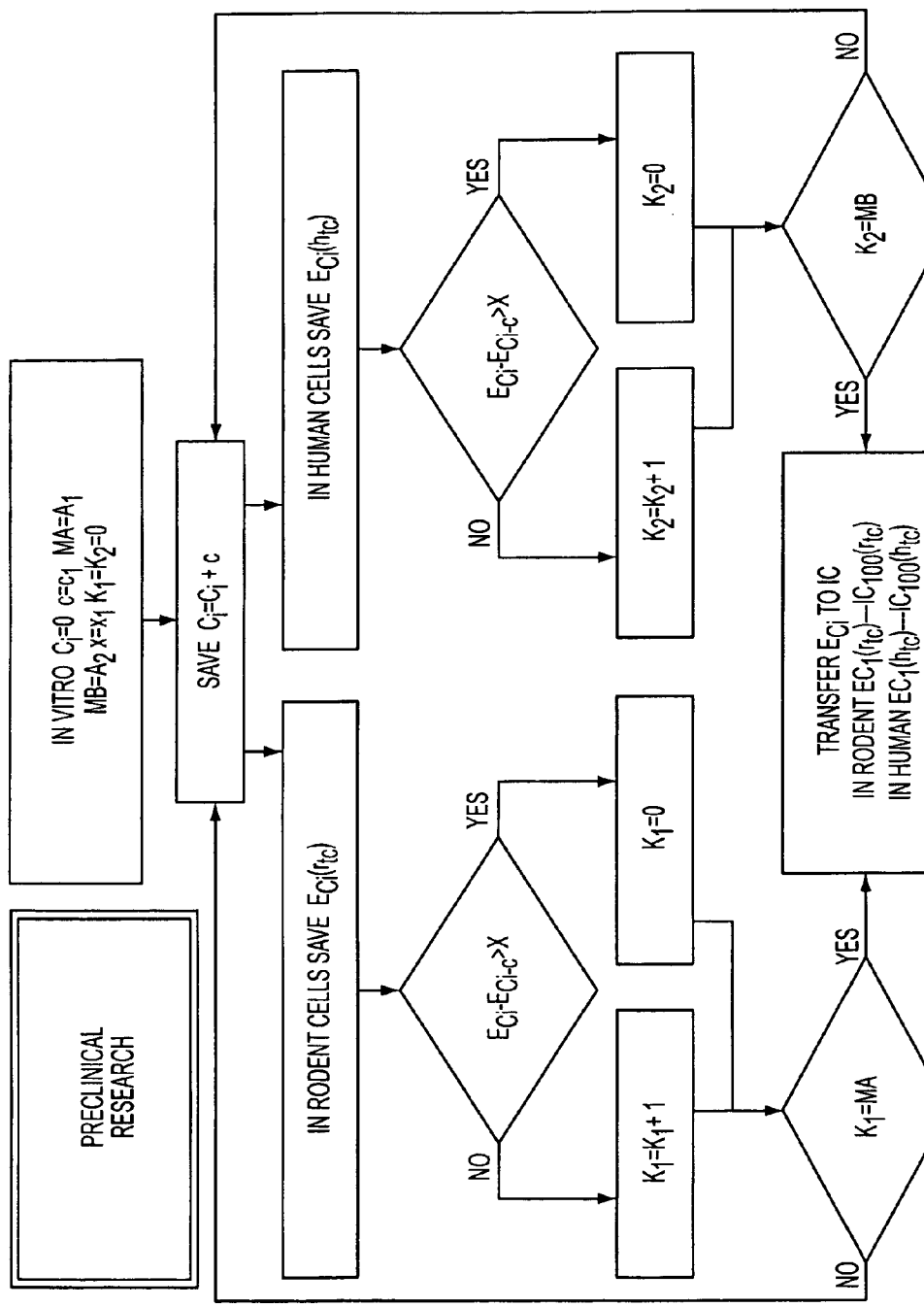
FIG. 5A shows a panel of an example implementation of the disclosed interactive trial design in the preclinical research stage

FIG. 5A shows an example implementation of the phase of pre-clinical research where the pharma company checks the in vitro effect of the drug concentrations in human cells and in rodent cells. The idea is to escalate the dose until there is no additional effect.

Figure 5B:
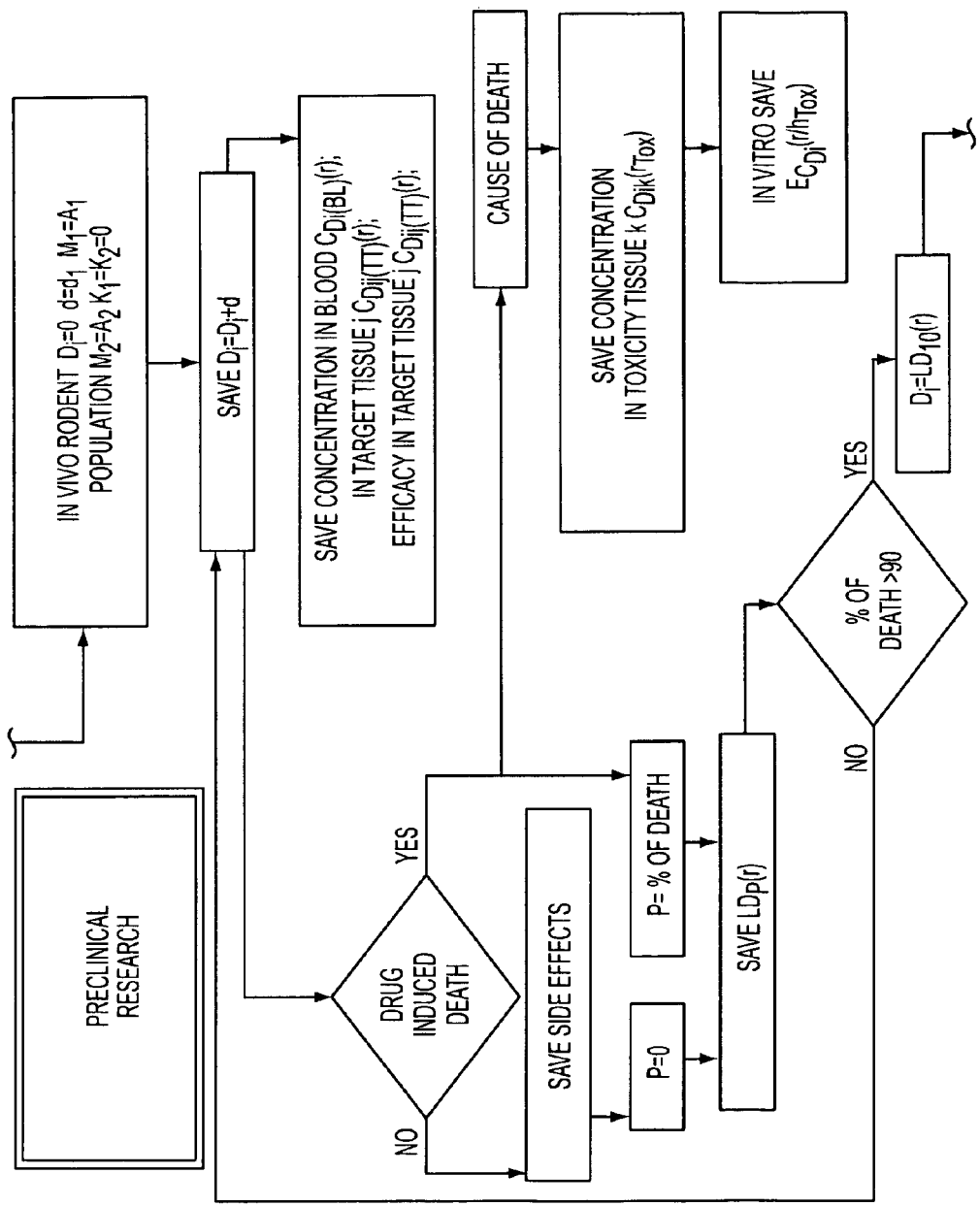
FIG. 5B shows a panel of an example implementation of the disclosed interactive trial design in the preclinical research stage (con't)

FIG. 5B shows an example implementation of the phase of pre-clinical research where the pharma company checks the in vivo effect of the drug concentrations in rodents. The idea is to calculate the LD10(r) in rodents. Since the work in done in vivo, if animal death is observed, then at least the reason for the lethal effect can be partially clarified by calculating the effect of the drug administered at dose "i" in rodent or human toxicity tissue "k", i.e. ECDik(r/htox).

Figure 5C:
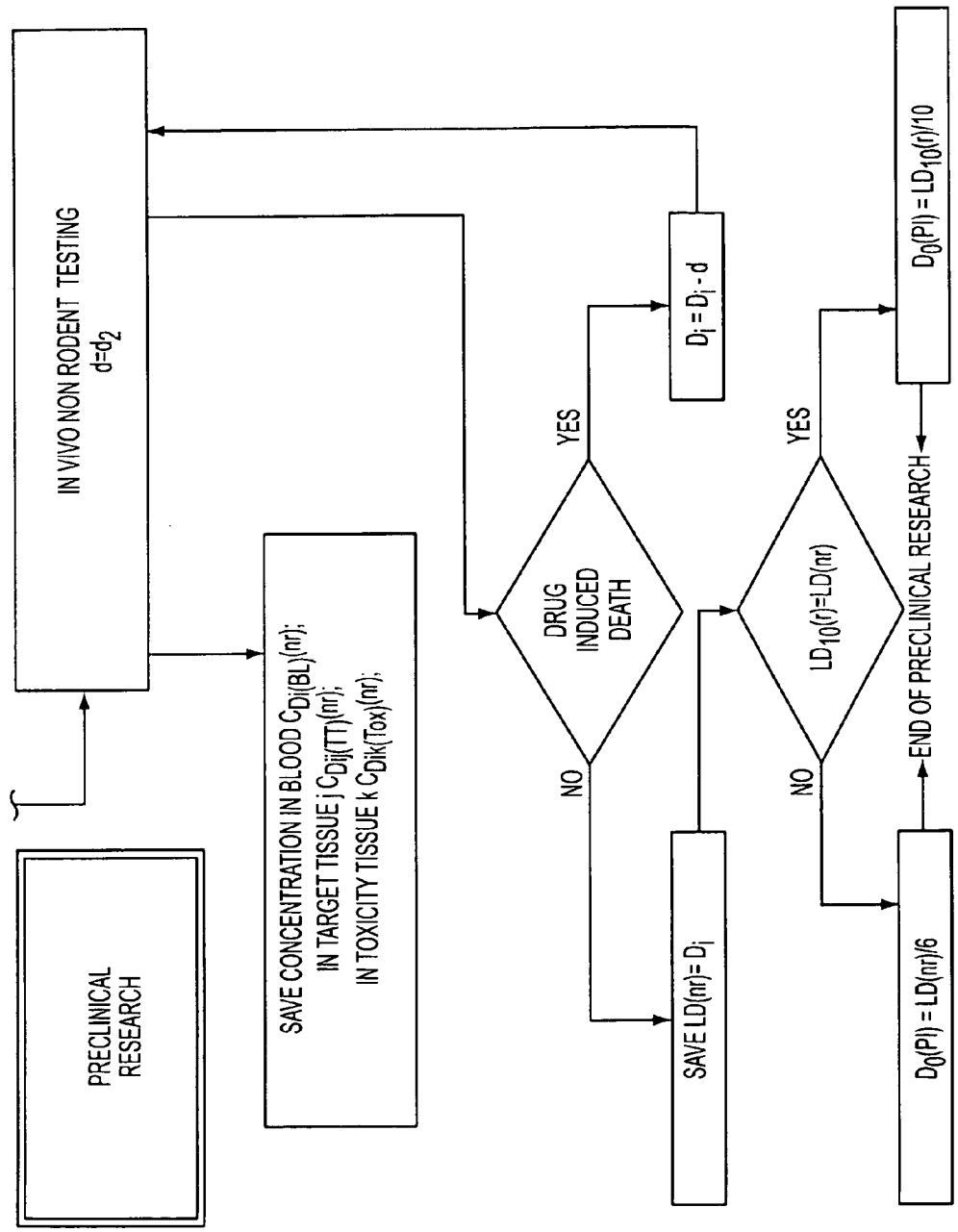
FIG. 5C shows one panel of an example implementation of the disclosed interactive trial design in the preclinical research stage (con't)

FIG. 5C shows an example implementation of the phase of pre-clinical research where the pharma company checks the in vivo effect of the drug concentrations in a nonrodent species. This is necessary in order to determine the initial dose of the drug (D0(PhI)) to begin Phase I clinical studies. The LD(nr) is calculated and compared to the LD10(r) and with this information D0(PhI) can be calculated.

Figure 5D:
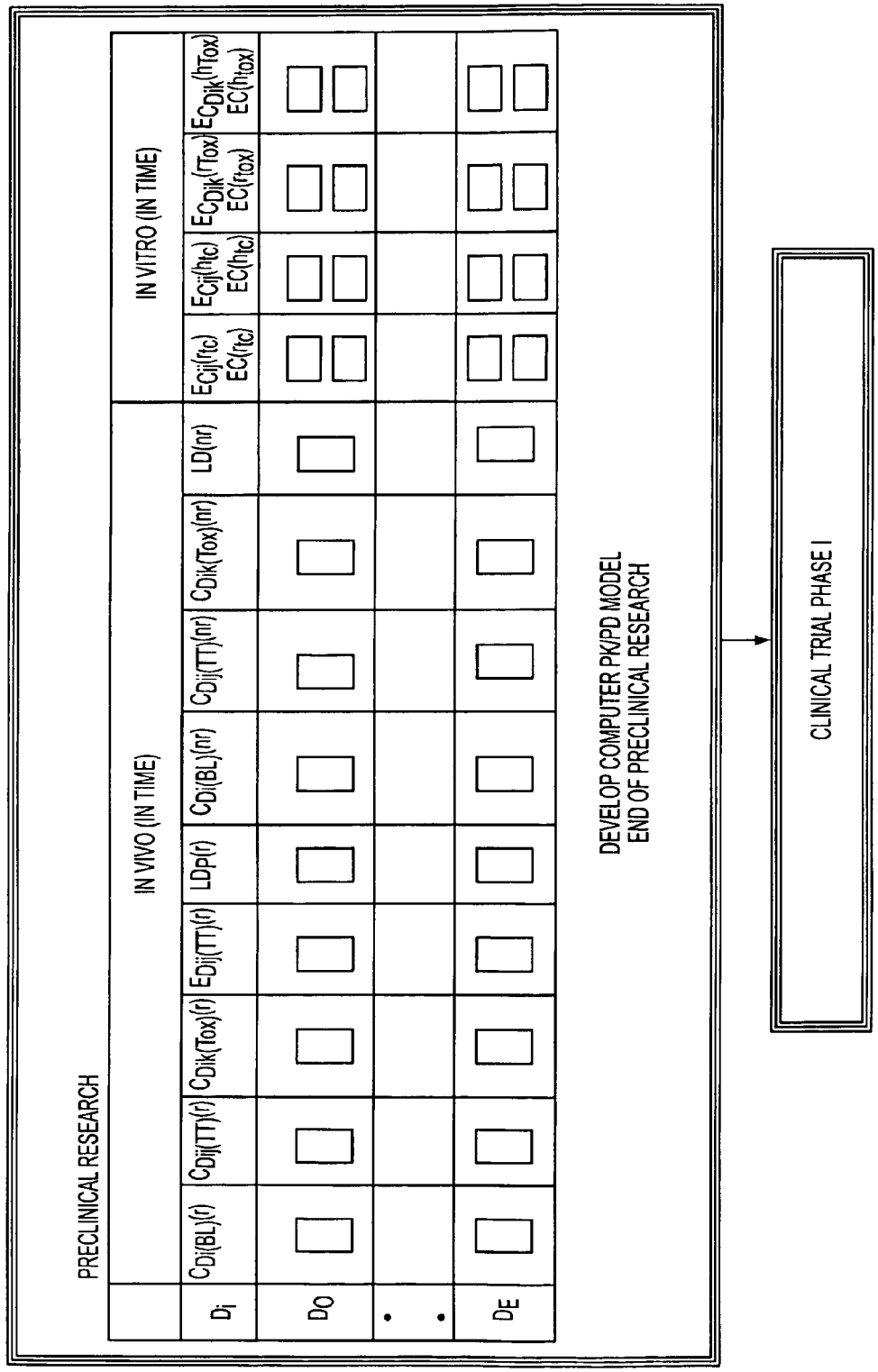
FIG. 5D shows a summary of the preclinical research stage

FIG. 5D shows a summary table of all the data used to develop the PK/PD model. The shaded boxes in the table stand for concrete numbers.

2. Phase-I: Finalizing and Validating the PK/PD Module

During dose escalation testing in the Phase-I trials, the computer model (in silico patient) interacts with the trial, predicting the results for every step in the trial and, at termination of every step, is updated by implementing the observed effect and toxicity. In this way the computer model (in silico patient) is continuously validated and fine-tuned, to give better predictions in the next step. This could, possibly, save steps during dose escalation, which is necessary for obtaining the toxicity profile and an initial efficacy profile. During Phase-I trials, while using the intra-patient dose escalation method, the model is provided with data on cumulative effect and cumulative toxicity, if observed.

In this way, by the end of Phase-I, a fully verified in vivo human model is available, integrating all the existing data on PK and PD of the drug.

Figure 5E:
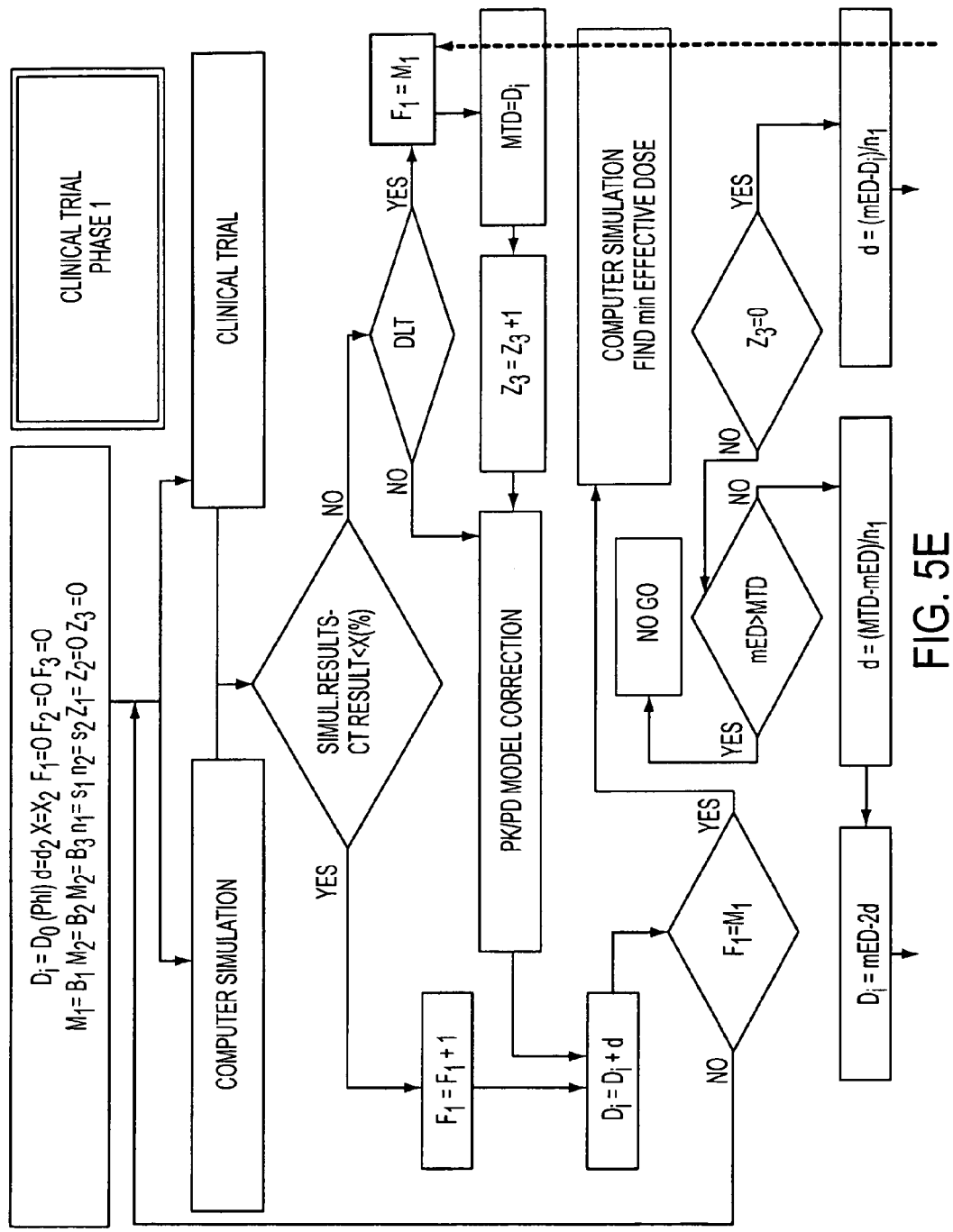
FIG. 5E shows one panel of an example implementation of the disclosed interactive trial design in the Phase I trial stage

FIG. 5E shows an example implementation of steps in Phase I clinical research where the pharma company performs the clinical trial in parallel to computer simulations. The on-line cooperation between pharma's clinical trial and simulations can greatly facilitate the determination of the minimal effective dose (mED). If it is seen in simulation that mED>MTD (maximum tolerated dose), then an early NOGO decision can be made. At the same time, an early calculation of the dose elevation increment of the drug, d, can be made. In addition, in this stage, if the simulation results show that the clinical trial (CT) results >a chosen threshold (X), then the PK/PD model can be adjusted.

Figure 5F:
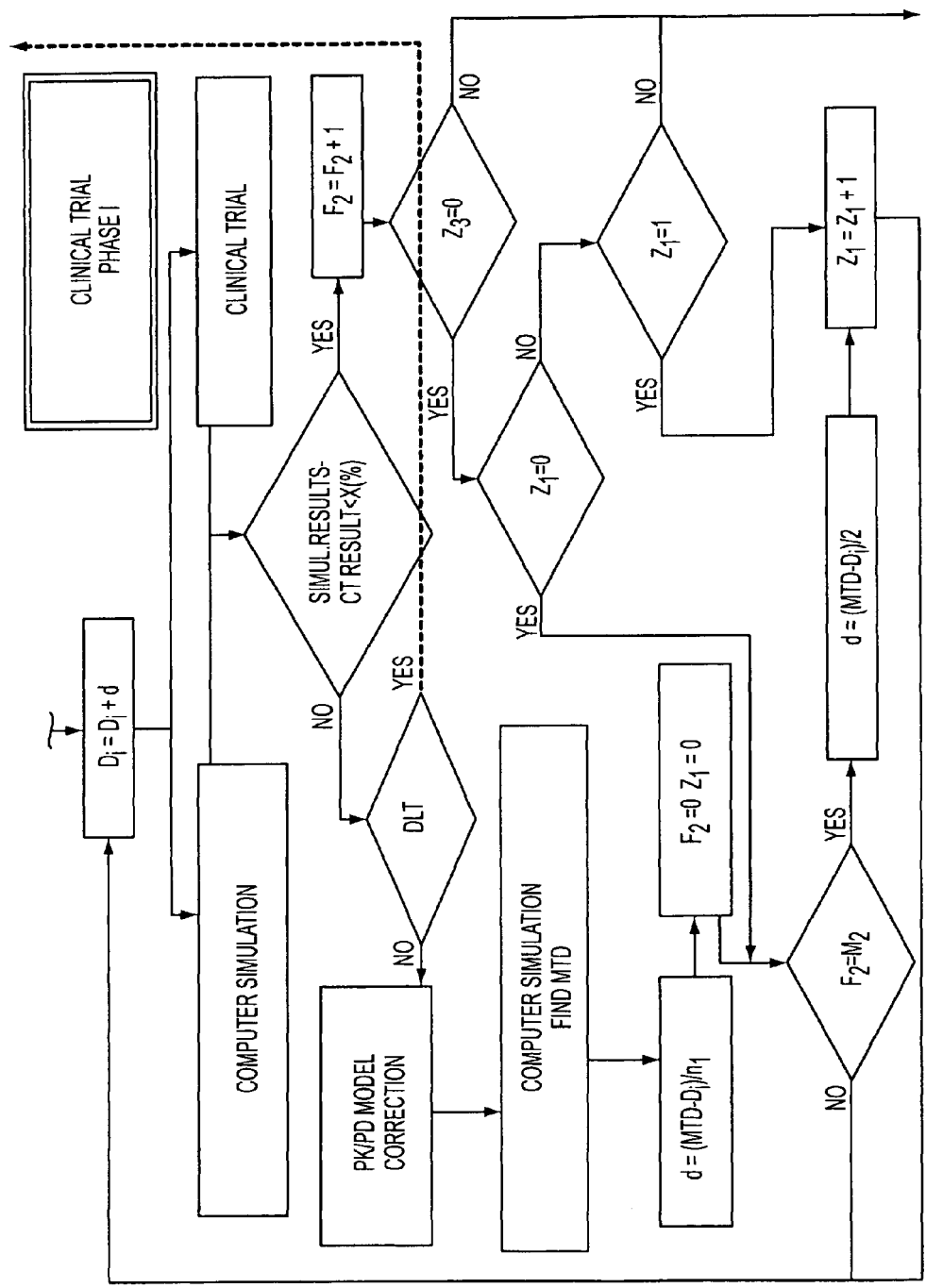
FIG. 5F shows one panel of an example implementation of the disclosed interactive trial design in the Phase I trial stage (con't)

FIG. 5F shows an example implementation of steps in Phase I clinical research where the pharma company performs the clinical trial on the drug in parallel to computer simulations based on the disclosed techniques. Here, the MTD is determined and again, at this point, the algorithm allows an early determination of the dose escalation step, d. In addition, in this stage, if the simulation results show that the clinical trial (CT) results >a chosen threshold (X), then the PK/PD model can be adjusted.

Figure 5G:
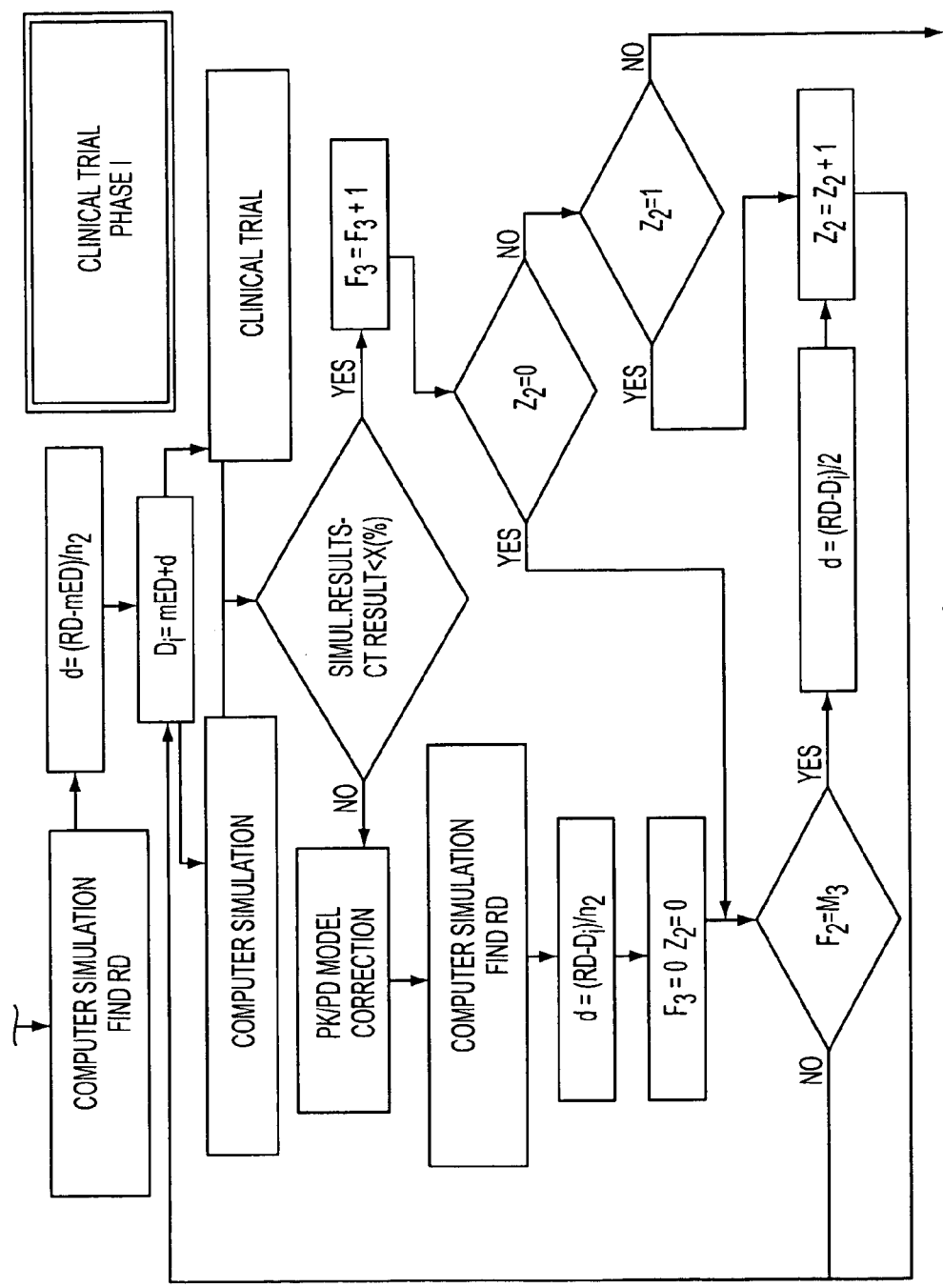
FIG. 5G shows one panel of an example implementation of the disclosed interactive trial design in the Phase I trial stage (con't)

FIG. 5G shows an example implementation of steps in Phase I clinical research where the pharma company performs the clinical trial on the drug in parallel to computer simulations based on the disclosed techniques. Here, the algorithm allows an early determination of the recommended dose (RD). Here again, the dose escalation step (d) is calculated. In addition, in this stage, if the simulation results show that the clinical trial (CT) results >a chosen threshold (X), then the PK/PD model can be adjusted.

Figure 5H:
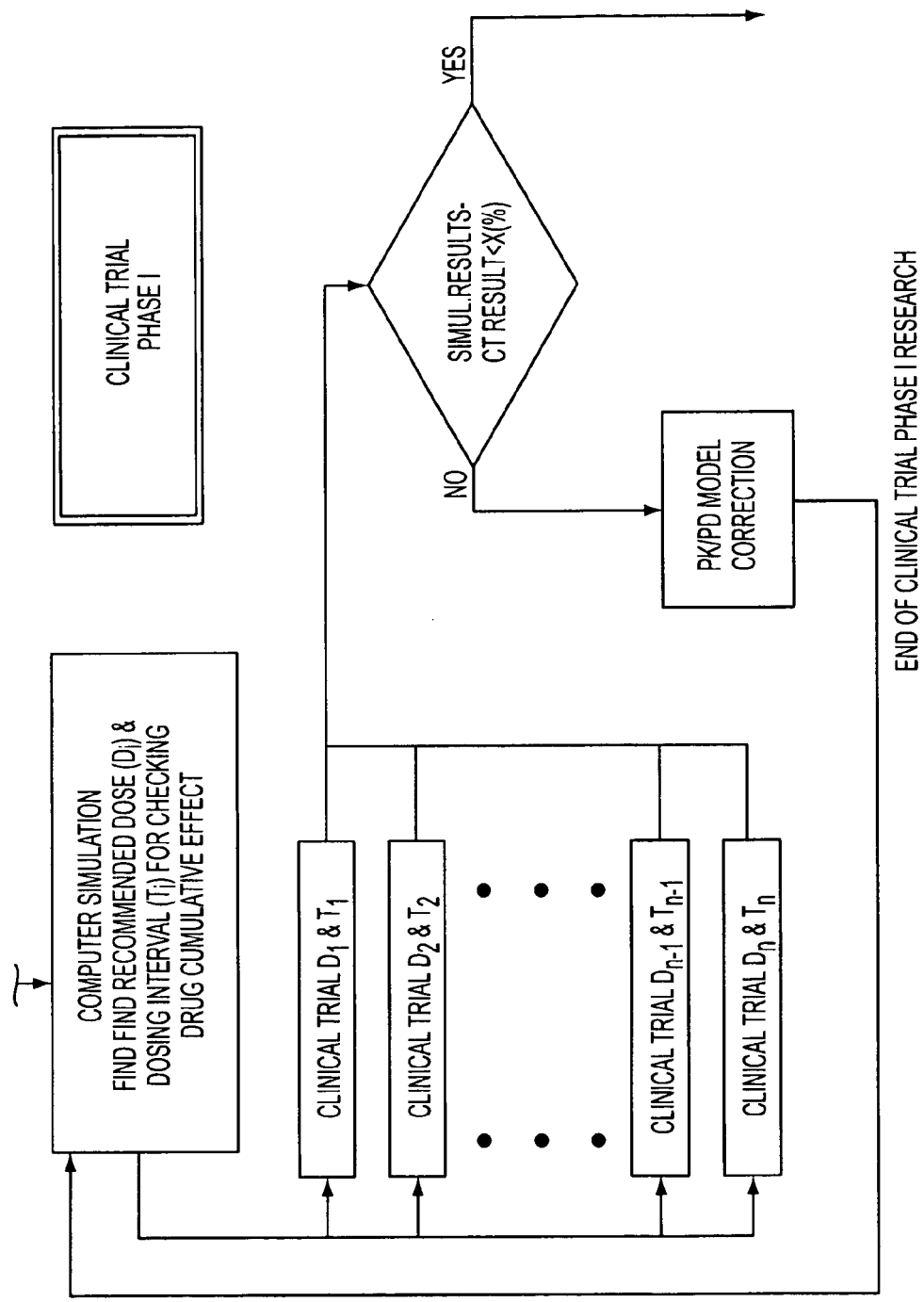
FIG. 5H shows one panel of an example implementation of the disclosed interactive trial design in the Phase I trial stage (con't)
Figure 51:
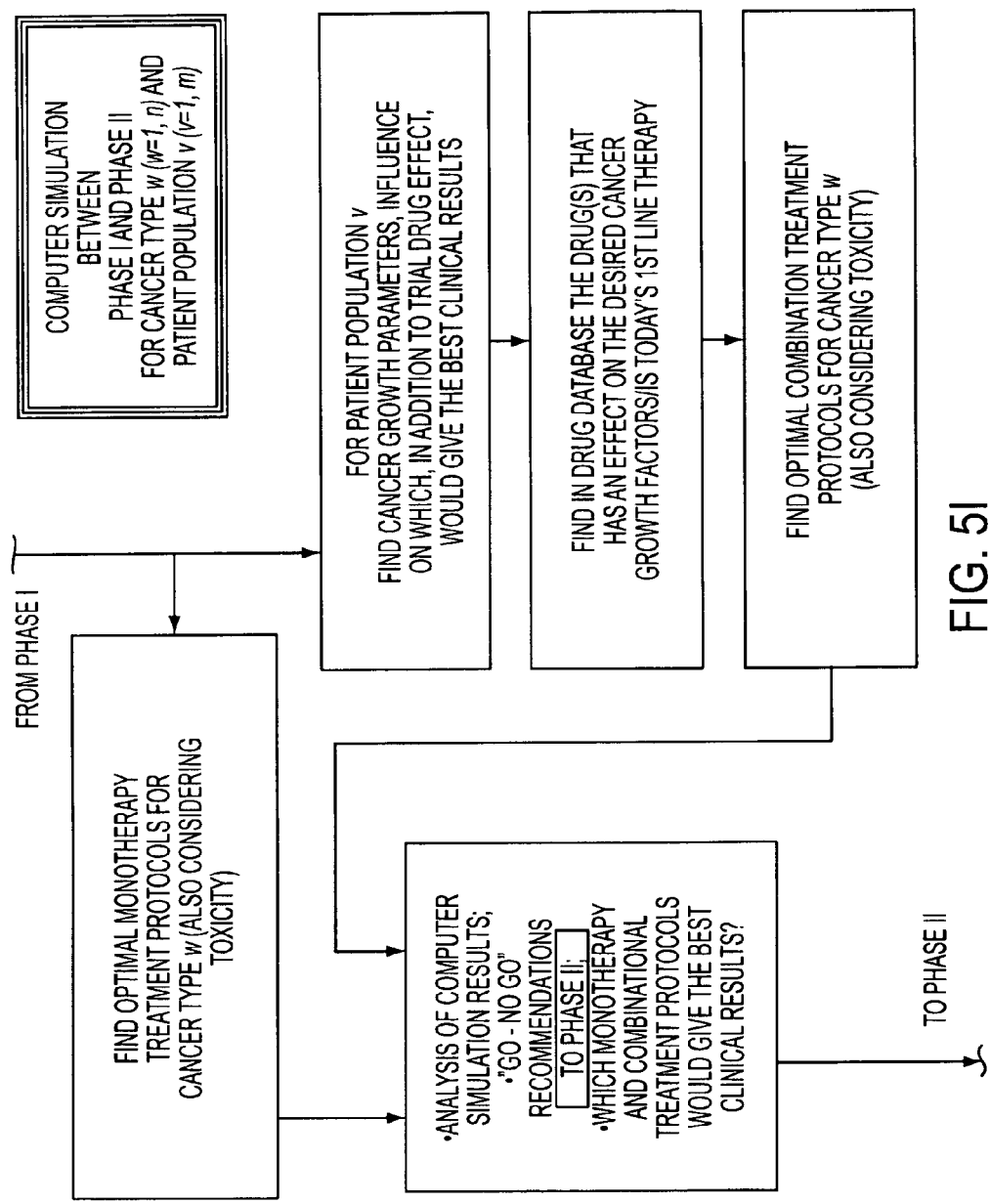

At this point, the PK/PD model is completed. Also, MTD, mED and RD have already been calculated. Now, as shown in FIG. 5H many simulations are performed with different doses and dosing intervals. With these parallel virtual trials, the drug's cumulative effect is checked and again, if the simulation results show that the clinical trial (CT) results >a chosen threshold (X), then the PK/PD model can be adjusted as necessary.

3. Interim Stage Between Phase-I and Phase-II: Intensive Simulations of Short-Term Treatments Following Phase-I the model can yield reasonable, short-term predictions concerning the effects of definite drug administration schedules on disease progression for specific indications. This allows one to perform an exhaustive search in the protocol space (i.e., within all the treatment schedule possibilities), for those mono- and combination therapy schedules, which are expected to yield the highest response and lowest toxicity for any potential cancer type to be treated. This may help the drug developer to predict the most effective treatment schedule and the most promising indication, thus saving patient health, and time and costs of the drug's development.

FIG. 5I shows example implementations of steps in between Phase I and Phase II. At this point, many simulations are carried out with different cancer types in order to find the optimal protocol for different patient populations and different indications. The optimized result can then be compared with the first line therapy. At the end of this step, one can recommend which indications and patient populations to continue with to Phase III. Lastly, a GO-NoGo decision can be made at this point.

4. Phase-II and Phase-III: Focusing the Clinical Trials

At the onset of Phase-II trials and following the interim stage outlined in section 3, a few proposed treatment schedules for the selected indication(s) are applied in short pilot trials testing a relatively small number of patients. After the first results are obtained (supposedly 6 months on average), the model should be adjusted by implementing the new data on the observed effects (including that indicated by surrogate markers).

Subsequently, a new set of intensive simulations is carried out, predicting disease progression during an extended period of up to two years, and predicting which of the schedules, tested in short-term trials, are expected to yield the best results in the long-run (changes can be made to the schedules in accordance with the model predictions). At this stage the predicted effect for each selected schedule is compared with that of existing therapies for the same indications. The model allows personalization for the patients involved in the study, based on the results obtained after the first 6 months, to yield more precise predictions.

At this stage, the model can predict failure, that is, recommend a NoGo decision, for the drugs that are incapable of demonstrating benefit over the existing therapies. The schedule(s) predicted to carry the most significant benefit over the existing treatments are selected for further testing in Phase-III. After the efficacy and safety profile of the selected schedule(s) is confirmed in further Phase-II trials (for another 6 months), the selected schedules should be further tested in extended group of patients as Phase-III trials.

Figure 5J:
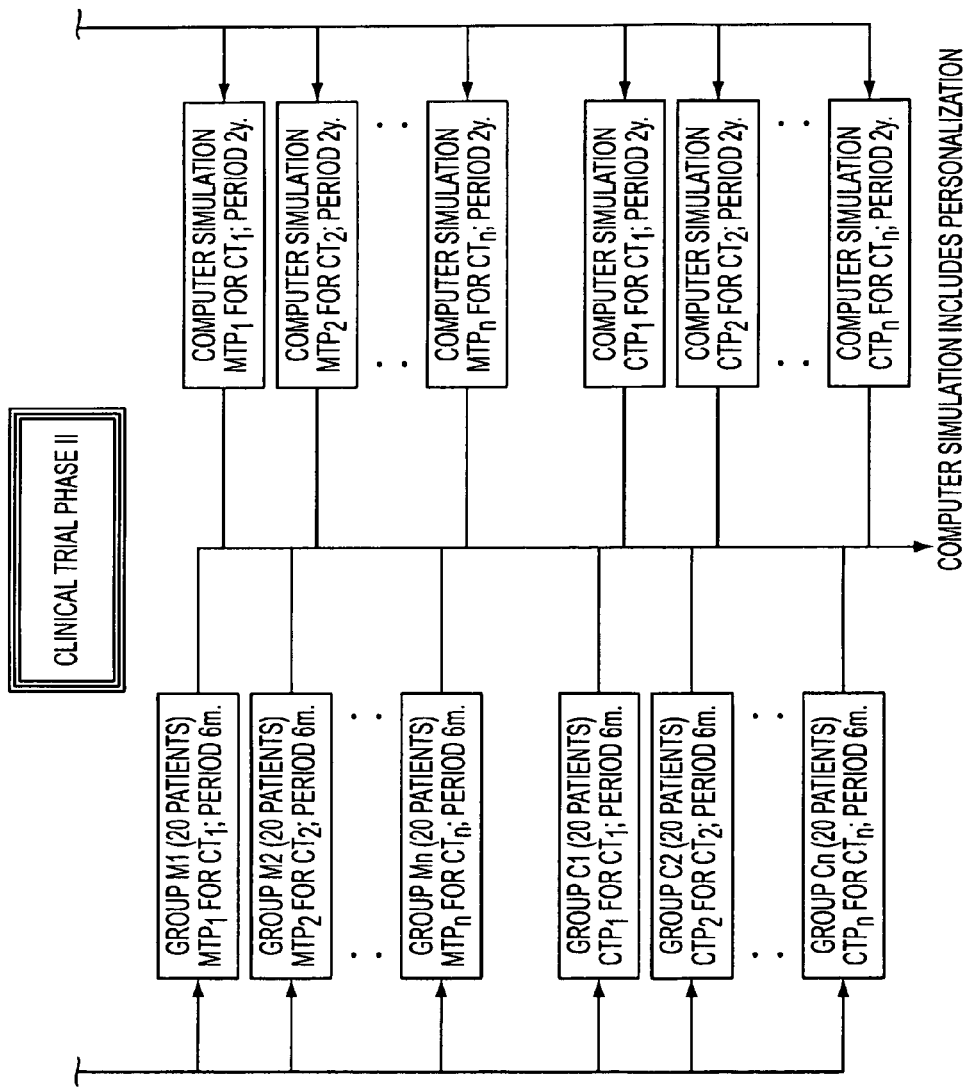
FIG. 5J shows one panel of an example implementation of the disclosed interactive trial design in the Phase II trial stage.

FIG. 5J shows an example implementation of steps of Phase II clinical research where the pharma company performs a series of small clinical trials in parallel with small numbers of patients. Recommendations from the model are tested in these trials. From this group of clinical trials, the interim results at 6 months are analyzed and long term computer simulations (simulated for a period of 2 years) are performed. From all of these small parallel clinical trials, the most promising are chosen to continue for another 6 months in parallel.

Figure 5K:
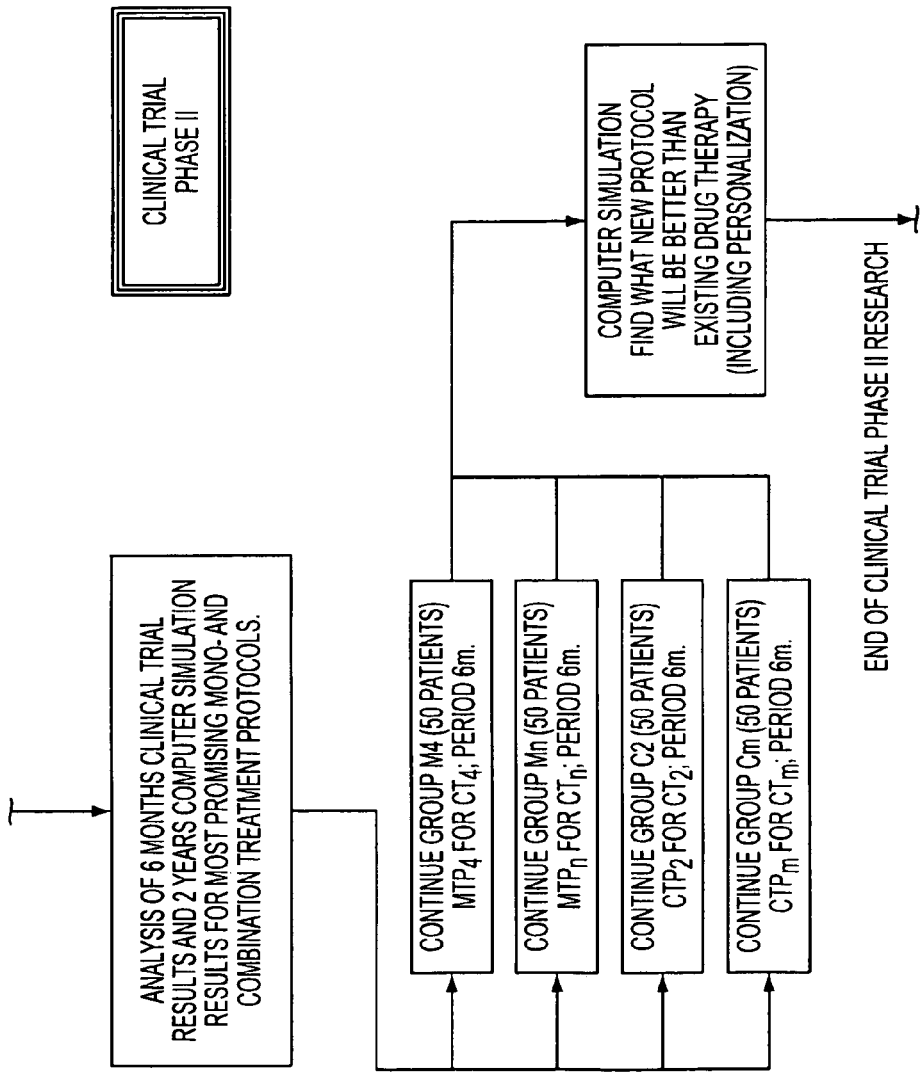
FIG. 5K shows one panel of an example implementation of the disclosed interactive trial design in the Phase II trial stage (con't)

As shown in FIG. 5K Phase II is continued with the most promising trials in parallel for another 6 months. Again, there is another round of data analysis, long term simulations and finally, the optimal protocol is chosen to continue to Phase III studies.

Figure 5L:
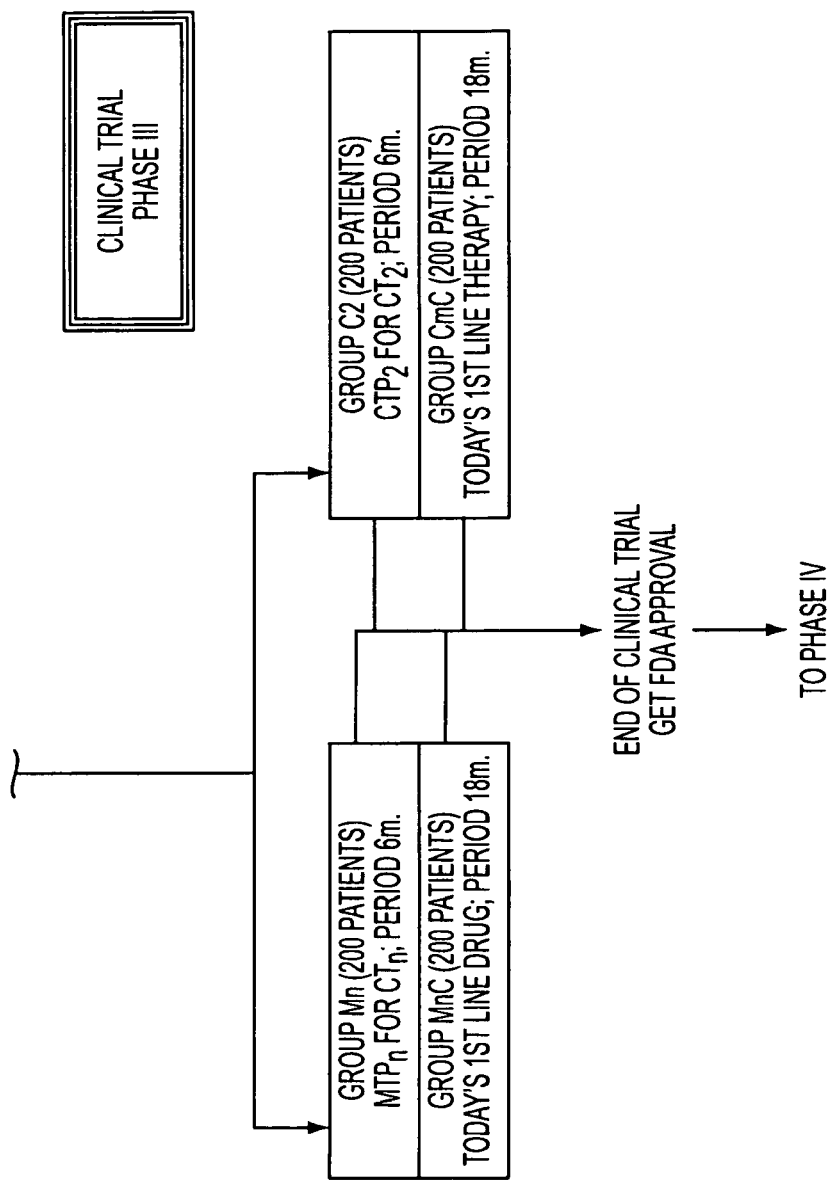
FIG. 5L shows one panel of an example implementation of the disclosed interactive trial design in the Phase III trial stage.

Further, as shown in FIG. 5L Phase III studies are carried out in a large number of patients and compare the test drug to standard therapy. The disclosed techniques thereby streamline the clinical development process by combining Phase II and III and efficiently contribute to an expedited FDA submission.

Figure 1:
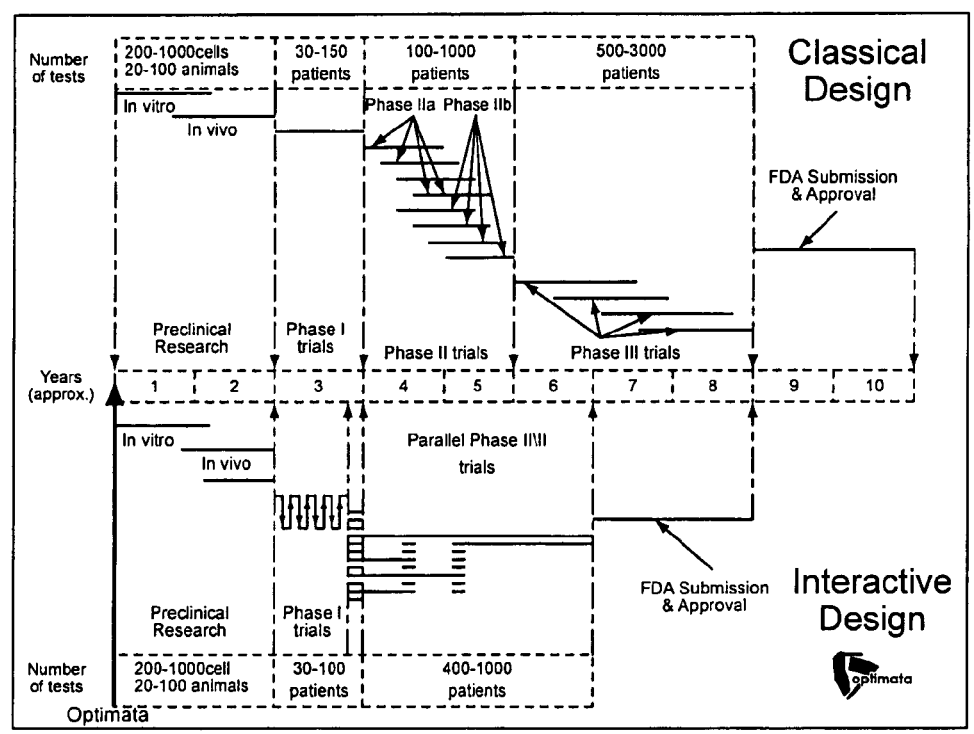
FIG. 1 shows duration and number of patients (averages) to be engaged in the Interactive Clinical Trial Design as compared to those in the classical design FIG. 2A A classical clinical trial protocol for drug "O" as compared to an example implementation of the disclosed interactive clinical design protocol based on stages of implementing an example implementation of the disclosed teachings.
Figure 2A:
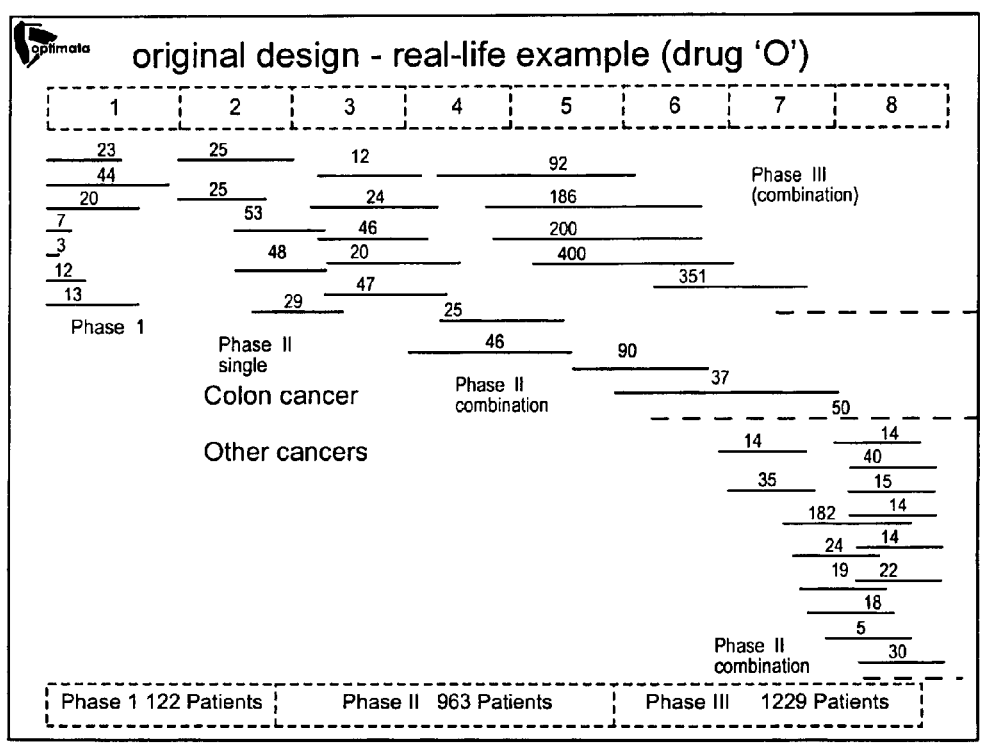
FIG. 2B-E various stages of an example implementation.
Figure 2B:
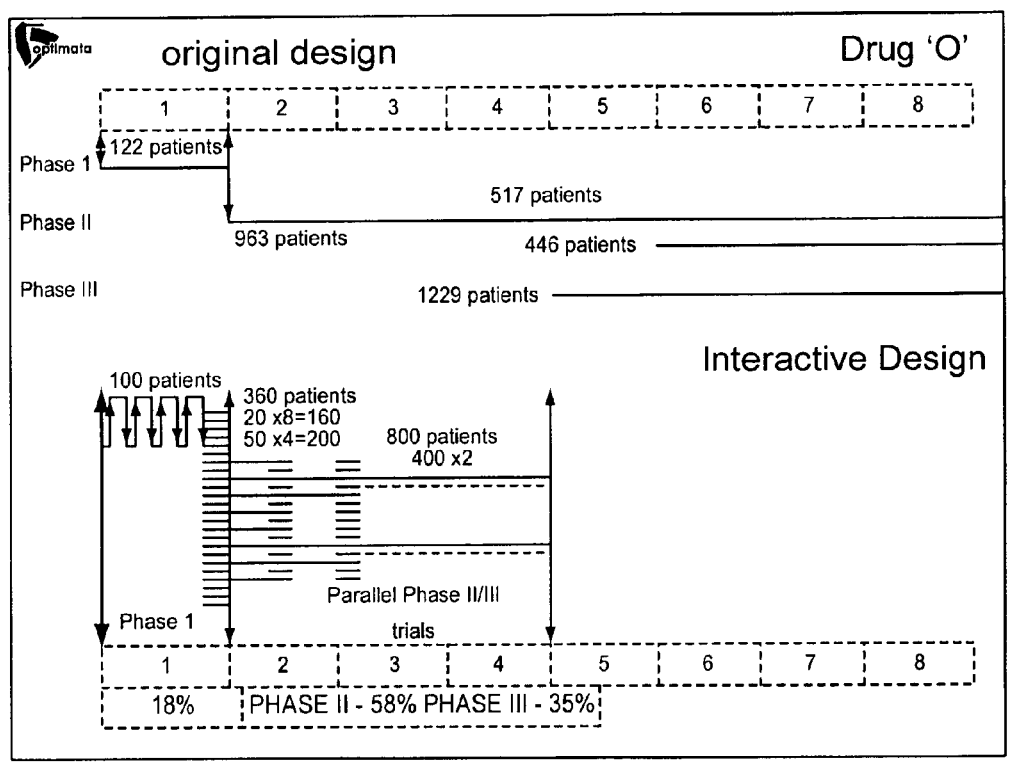
Figure 2C:
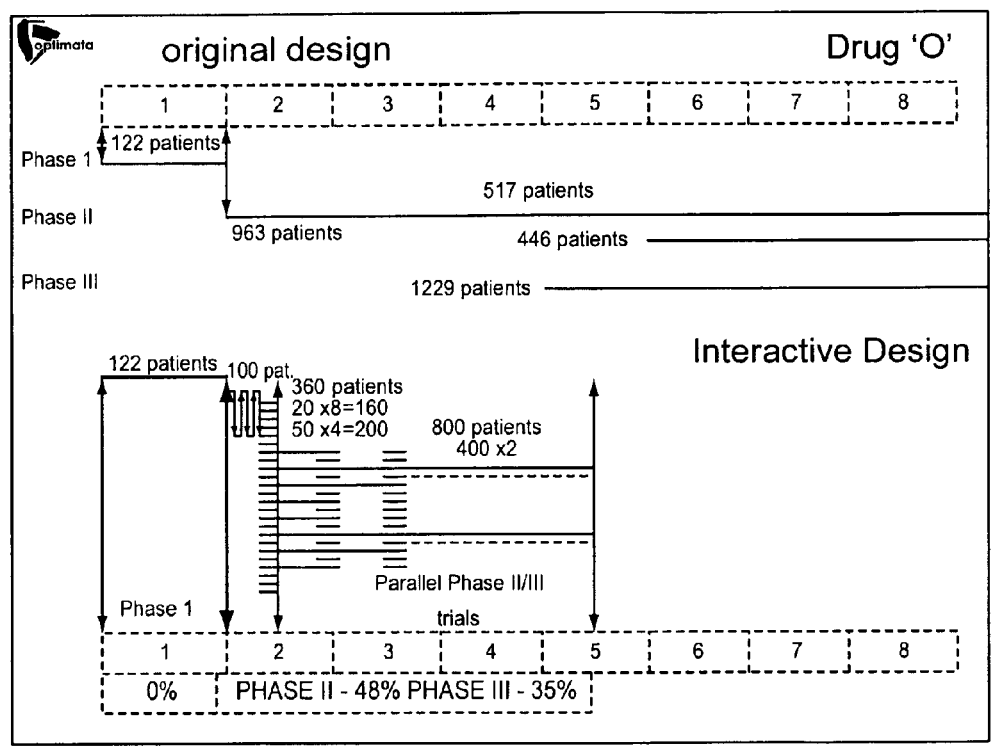
Figure 2D:
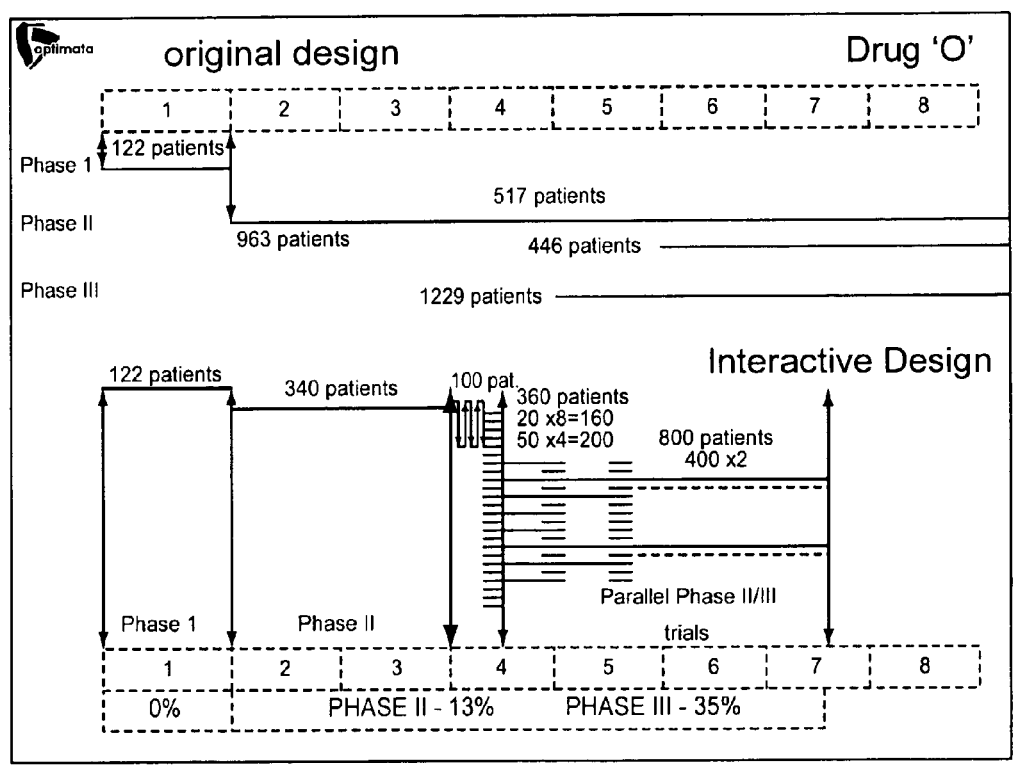
Figure 2E:
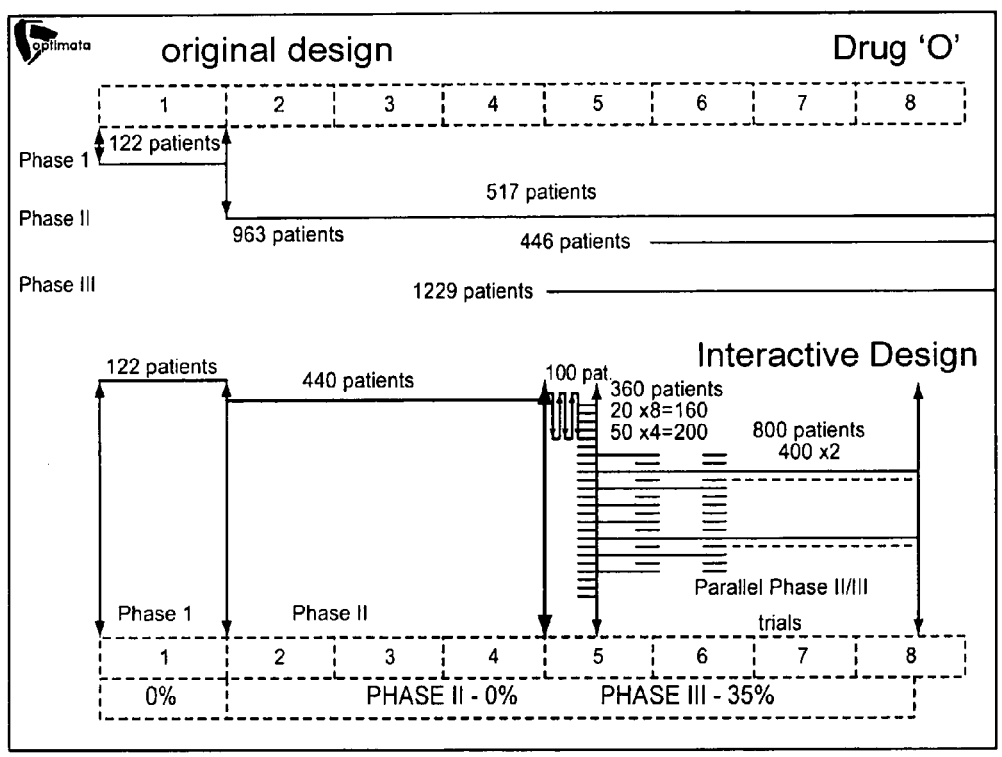
Figure 5M:
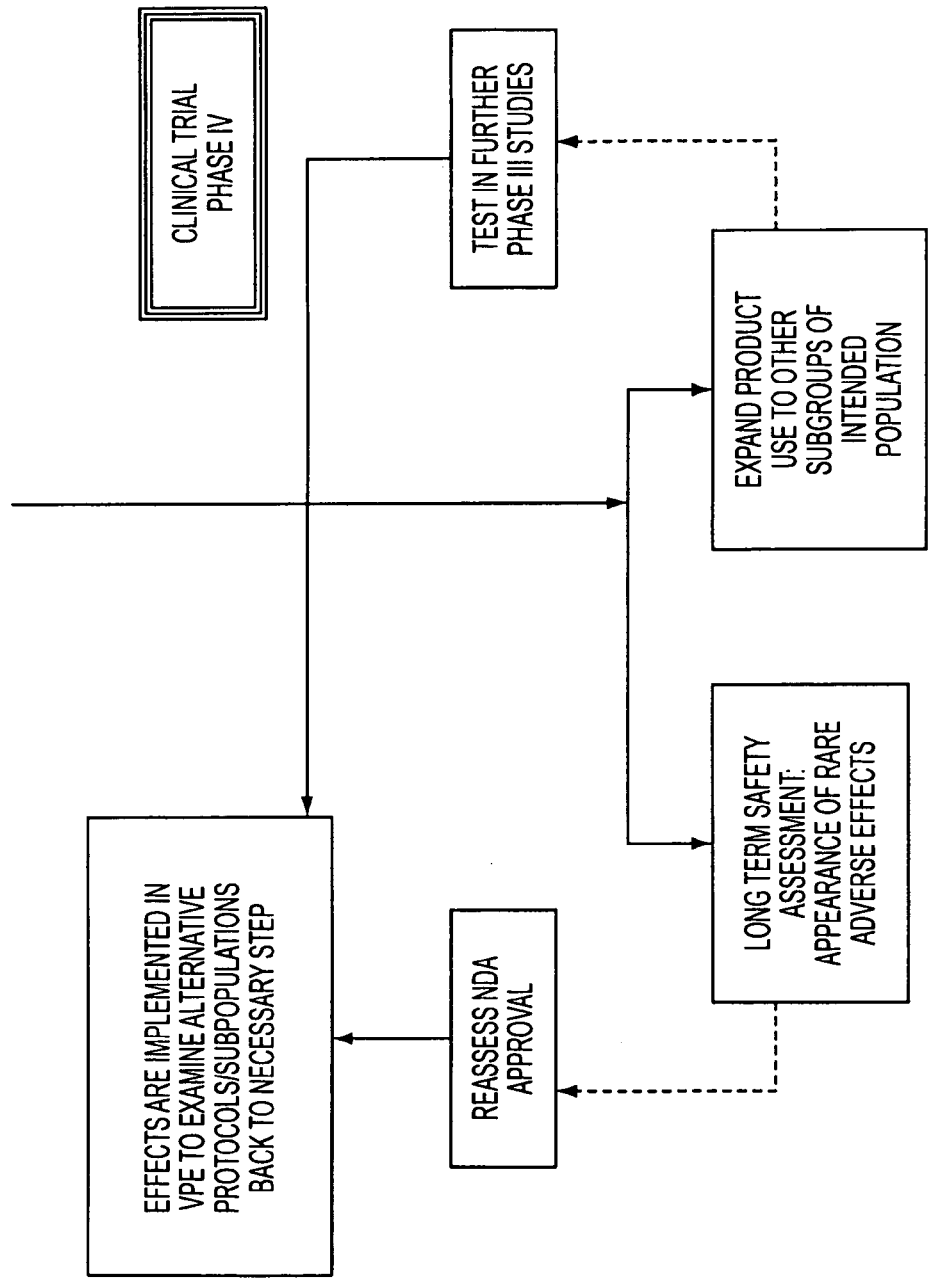
FIG. 5M shows one panel of an example implementation of the disclosed interactive trial design in the Phase IV trial stage.

Finally, as shown in FIG. 5M, Phase IV studies are carried out after market approval and long term safety assessment and subpopulation analyses are carried out in the virtual patient engine (VPE). If rare side effects or unexpected drug interactions are found in certain subpopulations, then the disclosed technique can recommend to which step the developer should go back to in order to improve drug performance The example implementation of the interactive clinical trial design was compared to a classical clinical trial design of anti-cancer drugs (denoted original). FIG. 1 illustrates the average differences in the number of patients expected to be engaged in the clinical trials designed according to each of the two methods.

One can notice in this figure a significant predicted saving in time and in the number of patients, which the technique of interactive clinical trials design offers. FIGS. 2A-2E schematically present the results of the theoretical comparison between the classical design in the development of a test drug "0", currently in Phase II-III in one of the big Pharma companies and the design of the same drug under the interactive clinical trials technique; the differences (in percentage) in the number of patients and the total duration of drug development are noted at the bottom of FIGS. 2B-2E.

Interactive Clinical Trial Design as Compared to the Adaptive Trial Design Method "Adaptive designs are dynamic". They are based on the assumptions of Bayesian statistics (in contrast to the classical design, which is based on frequentists assumptions). Adaptive design trials suggest an improvement to the classical design, as they offer ability to stop trials relatively early, drop or add treatment groups, change group proportions or shift seamlessly into a later phase, etc. These models aid in planning trials by predicting the probability distribution of trial outcomes conditional on current knowledge and assumption, and thus evaluating the ability of the trial to support a certain decision. These models rely upon prior probability distribution (e.g. FIG. 3) [30-33].

Figure 3:
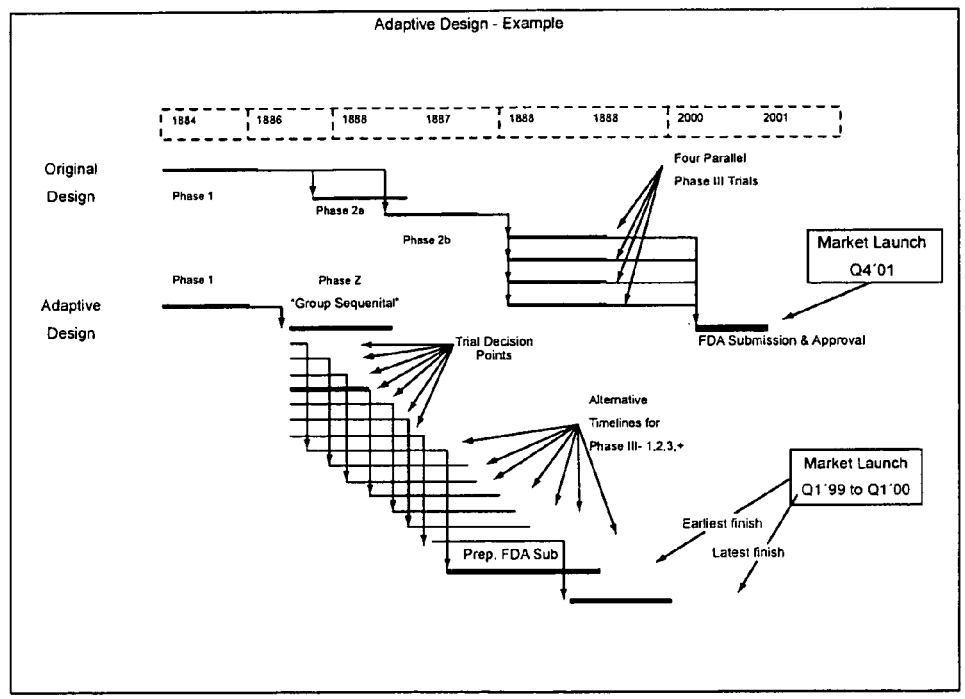
FIG. 3 shows an example of adaptive trial design as compared to the classical design.

By comparing FIG. 3 to FIG. 1, one can immediately notice the main differences between the two methods: (a) the point of influence of the Interactive Design can be as early as the Pre-clinical stage, whereas to the point of influence of the Adaptive Design begins only in Phase-II; (b) moreover, while the first and potentially most important decision-making impact of the Interactive Trial Design takes effect already at the end of Phase-I, the Adaptive Trial design's impact can be effectuated only towards the end of Phase-III. The reason for these differences lies in the significant distinction between the tools employed by each of the designs. A major asset offered by the disclosed technique is its predictive power, rather than the improved data analysis methods, offered by the Adaptive Design. In other words, the disclosed design is primarily prospective, integrating all the available biological, medical, pharmacological, theoretical and clinical information. In contrast, Adaptive design is primarily retrospective, integrating statistical methods with the information from the clinical trials Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A method of performing interactive clinical trials for testing a new drug for cancer related studies, resulting in clinical trial designs, the method comprising:
   a) performing a pre-clinical phase in which a computer model for pharmacodynamics of a drug is determined;
   b) obtaining data to determine the computer model for the pharmacodynamics of the drug of (a) from in vitro studies of the effect of the drug in animal cells, and optionally, in vivo studies in animals, and obtaining data for the pharmacokinetics of the drug of (a) from in vivo studies in animals;
   c) performing a phase I clinical trial in which a clinical trial on at least a single dose of the drug of (a) is administered to at least one human, and the phase I clinical trial is performed in parallel by performing computer simulations using the computer model constructed in step (a);
   d) adjusting the computer model based on comparison of the results of the clinical trial and computer simulations using the computer model, wherein the at least a single dose of step (c) is incrementally increased in at least one dose escalation step;
   e) calculating the dose escalation step by the computer simulations performed using the computer model in step (d) to obtain a maximal tolerated dose, minimum effective dose, and a recommended dose;
   f) checking the patient for cumulative drug effects after administration and providing this information to the computer model;
   g) performing multiple simulations using the computer model with different doses and dosing intervals for different indications and patient populations;
   h) determining, based on step (g) simulations results, an optimal regimen for the most responsive patient populations and clinical indications for a phase II clinical trial;
   i) performing at least one phase II clinical trial where a number of small scale clinical trials are performed in parallel in order to test the optimal treatment regimen from step (h) for different pairs of clinical indications and patient populations;
   j) performing at least one phase III clinical trial for a clinical indication chosen in step (h) using a regimen that was chosen in step (i); and
   k) performing at least one phase IV clinical trial, based on, at least, one previous clinical trial, for post-marketing subpopulation analysis that may identify differences in efficacy and toxicity between the subpopulations, and long term product safety assessment.

2. The method of claim 1, wherein in step (c), computer simulations of the model are performed prior to the phase I clinical trial, to predict results of the phase I clinical trial, and the predicted results are compared to the phase I clinical trial results and the computer model is adjusted based on the comparison.

3. The method of claim 1, wherein a first decision whether to continue the phase II clinical trial is made prior to step (i), stopping the trial if an adverse decision is made.

4. The method of claim 3, wherein in step (j), the most promising trials are chosen for clinical indications most sensitive to the drug administered via the most efficient regimen.

5. The method of claim 4, wherein in step (j), a second decision whether to continue the phase III clinical trial is made, stopping the trial if an adverse decision is made.

6. The method of claim 5, wherein the second decision is based on a prediction of safety profile of the new drug in the most promising trial compared with safety of pre-existing therapies.

7. The method of claim 5, wherein the decision is based on a prediction of efficacy profile of the drug in the most promising trial compared with efficacy of pre-existing therapies.

8. The method of claim 1, wherein results of step (h) are used to define clinical indications and define sub-groups of patients most sensitive, susceptible and responsive to the drug.

9. The method of claim 8, wherein an effective treatment regimen is defined for a subset of the subgroups.

10. The method of claim 1, wherein the computer model is adjusted based on whether the clinical trial indicates a result higher than a threshold in at least one of pre-clinical, phase I and phase II trials.

11. The method of claim 1, wherein in step (i), the small-scale clinical trials are performed in parallel for a chosen clinical indication by a chosen treatment regimen.

12. The method of claim 1, wherein step (k) is performed to prove safety of the drug.

13. The method of claim 1, wherein step (k) is performed to prove efficacy of the drug.

14. The method of claim 1, when hitherto unknown effects are discovered in step (k), the computer model is adjusted to obtain predictions for new regimens, patient populations and clinical indications.

15. A method of performing interactive clinical trials for a new drug for cancer related studies, resulting in clinical trial designs, the method comprising a step of administering at least a single dose of a drug in vitro or in vivo to obtain data for a pre-clinical phase in which a computer model for pharmacokinetics and phramacodynamics is created and adjusted based on data from in vitro studies and optionally in vivo studies in animals, wherein that pre-clinical phase is performed in parallel with simulated computer predictions, and wherein the simulated computer predictions are compared with the pre-clinical results and the comparison is used to adjust the computer model, wherein the computer model is an in silico patient that is adjusted according to the results of the pre-clinical trials.

16. The method of claim 15, wherein the computer model adjusted according to the results of the pre-clinical trials is used in the design of further pre-clinical trials.

17. A method of performing interactive clinical trials for a new drug for cancer related studies, resulting in clinical trial designs, the method comprising a step of obtaining data from administration of a drug in a dose-escalation during phase I clinical trial performed in parallel with simulated computer predictions, and wherein the simulated computer predictions are compared with clinical results and the comparison is used to adjust the computer model, wherein the computer model is an in silico patient that is adjusted according to the results of the clinical trials.

18. A method of performing interactive clinical trials for a new drug for cancer related studies, resulting in clinical trial designs, the method comprising: a step of administering at least a single dose of a drug to obtain data to develop a strategy for a phase I clinical trial wherein the phase I clinical trial is performed in parallel with simulated computer predictions, and wherein the simulated computer predictions comprise using a computer model that is an in silico patient that is adjusted according to the results of the clinical trials.

19. A method of performing interactive clinical trials for a new drug for cancer related studies, resulting in clinical trial designs, the method comprising a step of administering at least a single dose of a drug to obtain data for performing a phase II clinical trial wherein at least one clinical trial is performed in parallel with simulations performed using a computer model, resulting in prediction of one or more trial outcomes,
  wherein the prediction of one or more trial outcomes is compared with clinical results from the phase II clinical trials and the comparison is used to adjust the computer model, wherein the computer model is an in silico patient that is adjusted according to the results of the clinical trials.

20. A method of performing interactive clinical trials for a new drug for cancer related studies; resulting in clinical trial designs, the method comprising a step of administering at least a single dose of a drug to obtain data for performing a phase III clinical trial in parallel with simulations performed using a computer model that predicts a better treatment for the design of further clinical trials, resulting in prediction of one or more trial outcomes,
  wherein the prediction is compared with clinical results from the phase III clinical trials and the comparison is used to adjust the computer model, wherein the computer model is an in silico patient that is adjusted according to the results of the clinical trials.

21. A method of performing interactive clinical trials for a new drug for cancer related studies, resulting in clinical trial designs, the method comprising a step of administering to a patient at least a single dose of a drug to obtain data for performing a phase IV clinical trial in parallel with simulations performed using a computer model that predicts post-marketing efficacy of a drug, and long term drug safety assessment, resulting in prediction of one or more trial outcomes,
  wherein the prediction is compared with clinical results from the phase IV clinical trials and the comparison is used to adjust the computer model, wherein the computer model is an in silico patient that is adjusted according to the results of the clinical trials.

* * * * *